(12) United States Patent
Zhang et al.

(10) Patent No.: US 11,117,898 B2
(45) Date of Patent: Sep. 14, 2021

(54) PYRAZOLO-HETEROARYL DERIVATIVE, PREPARATION METHOD AND MEDICAL USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Guobao Zhang, Shanghai (CN); Chunfeng Shu, Shanghai (CN); Qiyue Hu, Shanghai (CN); Feng He, Shanghai (CN); Weikang Tao, Shanghai (CN)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 198 days.

(21) Appl. No.: 16/464,341

(22) PCT Filed: Nov. 27, 2017

(86) PCT No.: PCT/CN2017/113007
§ 371 (c)(1),
(2) Date: May 28, 2019

(87) PCT Pub. No.: WO2018/095426
PCT Pub. Date: May 31, 2018

(65) Prior Publication Data
US 2021/0115046 A1   Apr. 22, 2021

(30) Foreign Application Priority Data
Nov. 28, 2016 (CN) .......................... 201611066071.7

(51) Int. Cl.
C07D 471/04 (2006.01)
A61K 31/395 (2006.01)
A61K 31/12 (2006.01)
C07D 487/04 (2006.01)

(52) U.S. Cl.
CPC ................. C07D 487/04 (2013.01)

(58) Field of Classification Search
CPC ..... C07D 471/04; A61K 31/395; A61K 31/12
See application file for complete search history.

(56) References Cited

FOREIGN PATENT DOCUMENTS

| | | |
|---|---|---|
| CN | 101917999 A | 12/2010 |
| CN | 102272134 A | 12/2011 |
| CN | 102666541 A | 9/2012 |
| KR | 10-2013-0112248 | 10/2013 |
| WO | 2002012224 A2 | 2/2002 |
| WO | 2005025583 A2 | 3/2005 |
| WO | 2007093901 A1 | 8/2007 |
| WO | 2008011406 A2 | 1/2008 |
| WO | 2008114008 A1 | 9/2008 |
| WO | 2009091032 A1 | 7/2009 |
| WO | 2010077613 A1 | 7/2010 |
| WO | 2010133882 A1 | 11/2010 |
| WO | 2011031965 A1 | 3/2011 |
| WO | 2012080730 A1 | 6/2012 |
| WO | 2015137887 A1 | 9/2015 |
| WO | 2015162075 A1 | 10/2015 |
| WO | 2016040419 A1 | 3/2016 |

OTHER PUBLICATIONS

Mahla et al, "Sweeten PAMPs: role of sugar complexed PAMPs in innate immunity and vaccine biology," Frontiers in Immunology, vol. 4, Article 248 (2013).
Diebold et al, "Innate Antiviral Responses by Means of TLR7-Mediated Recognition of Single-Stranded RNA," Science, vol. 303, pp. 1529-1531 (2004).
Lund et al, "Recognition of Single-Stranded RNA Viruses by Toll-Like Receptor 7," Proceedings of the National Academy of Sciences of the United States of America, vol. 101, No. 15, pp. 5598-5603 (2004).
Liu, "IPC: Professional Type 1 Interferon-Producing Cells and Plasmacytoid Dendritic Cell Precursors," Annual Review of Immunology, vol. 23, pp. 275-306 (2005).
Mikó et al, "Novel Nonimidazole Histamine H3 Receptor Antagonists: 1-(4-(Phenoxymethyl)benzyl)piperidines and Related Compounds," Journal of Medicinal Chemistry, vol. 46, No. 8, pp. 1523-1530 (2003).
Mikó et al, "Structural variations of 1-(4-(phenoxymethyl)benzyl)piperidines as nonimidazole histamine H3 receptor antagonists," Bioorganic & Medicinal Chemistry, vol. 12, No. 10, pp. 2727-2736 (2004).

(Continued)

*Primary Examiner* — Bruck Kifle
(74) *Attorney, Agent, or Firm* — Ice Miller LLP

(57) ABSTRACT

Disclosed are a pyrazolo-heteroaryl derivative, a preparation method and medical use thereof. In particular, this invention relates to a new pyrazolo-heteroaryl derivative as shown in the general formula (I), a preparation method thereof and a pharmaceutical composition containing the derivative and the use thereof as a therapeutic agent, in particular as a TLR7 agonist, wherein each substituent in the general formula (I) is defined in the description.

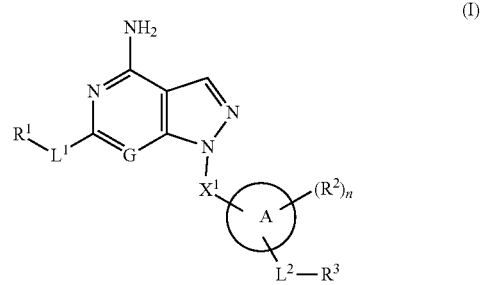

23 Claims, No Drawings

(56) References Cited

OTHER PUBLICATIONS

Int'l Search Report dated Feb. 26, 2018 in Int'l Application No. PCT/CN2017/113007.
PubChem Compound Summary (CID: 110171303), "1-[(2-Methoxy-5-nitrophenyl)methyl]-6-phenylpyrazolo[3,4-d]pyrimidin-4-amine," https://pubchem.ncbi.nlm.nih.gov/compound/110171303, pp. 1-8.
PubChem Compound Summary (CID: 110171269), "4-[(4-Amino-6-phenylpyrazolo[3,4-d]pyrimidin-1-yl)methyl]benzamide," https://pubchem.ncbi.nlm.nih.gov/compound/110171269#section=Substances-by-Category, pp. 1-8.
PubChem Compound Summary (CID: 11171264), "6-Phenyl-1[[4-Itrifluoromethyl)phenyl]methyl]pyrazolo[3,4-d]pyrimidin-4-amine," https://pubchem.ncbi.nlm.nih.gov/compound/110171264#section=Structures, pp. 1-8.
PubChem Compound Summary (CID: 110171260), "3-[(4-Amino-6-phenylpyrazolo[3,4-d]pyrimidin-1-yl)methyl]benzonitrile," https://pubchem.ncbi.nlm.nih.gov/compound/110171260#section=Related-Compounds, pp. 1-8.
PubChem Compound Summary (CID: 110171259), "2-[(4-Amino-6-phenylpyrazolo[3,4-d]pyrimidin-1-yl)methyl]benzonitrile," https://pubchem.ncbi.nlm.nih.gov/compound/110171259#section=Related-Records, pp. 1-8.
PubChem Compound Summary (CID: 110171256), "4-[(4-Amino-6-phenylpyrazolo[3,4-d]pyrimidin-1-yl)methyl] benzonitrile," https://pubchem.ncbi.nlm.nih.gov/compound/110171256#section=Substances-by-Category, pp. 1-8.
PubChem Compound Summary (CID: 110171258), "6-Phenyl-1[[4-(trifluoromethoxy)phenyl]methyl]pyrazolo[3,4-d]pyrimidin-4-amine," https://pubchem.ncbi.nlm.nih.gov/compound/110171258#section=Chemical-Vendors, pp. 1-8.

PYRAZOLO-HETEROARYL DERIVATIVE, PREPARATION METHOD AND MEDICAL USE THEREOF

CROSS-REFERENCE TO RELATED APPLICATION

This application is a Section 371 of International Application No. PCT/CN2017/113007, filed Nov. 27, 2017, which was published in the Chinese language on May 31, 2018, under International Publication No. WO 2018/095426 A1, which claims priority under 35 U.S.C. § 119(b) to Chinese Patent Application No. 201611066071.7, filed on Nov. 28, 2016, the disclosures of which are incorporated herein by reference in their entireties.

FIELD OF THE INVENTION

The present invention relates to a novel pyrazolo-heteroaryl derivative of formula (I), a method for preparing the same and a pharmaceutical composition comprising the same, as well as the use thereof as a therapeutic agent, particularly as a TLR7 agonist.

BACKGROUND OF THE INVENTION

Toll-like receptors (TLRs) are a class of important protein molecules involved in innate immunity. TLRs are single, membrane-spanning, non-catalytic receptors, usually expressed on sentinel cells such as macrophages and dendritic cells, and can recognize structurally conserved molecules produced by microbes. Once these microbes have broken through physical barriers such as the skin or intestinal tract mucosa, they are recognized by TLRs, which activate immune cell responses (Mahla, R S. et al., Front Immunol. 4: 248 (2013)). The ability of immune system to broadly recognize pathogenic microorganisms is, in part, due to the widespread presence of toll-like immunoreceptors (TLRs).

There are at least ten different TLRs in mammals. Ligands and corresponding signaling cascades have been identified for some of these receptors. TLR7 is a member of the subgroup of TLRs (TLRs 3, 7, 8, and 9), localised in the endosomal compartment of cells which are specialized to detect non-self nucleic acids. TLR7 plays a key role in anti-viral defense via the recognition of ssRNA (Diebold S. S. et al, Science, 2004: 303, 1529-1531; and Lund J. M. et al, PNAS, 2004: 101, 5598-5603). TLR7 has a restricted expression-profile in human, and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)), which are the primary type I interferon-producing cells secreting high levels of interferon-alpha (IFNα) and interferon-beta (IFNβ) in response to viral infections (Liu Y-J, Annu. Rev. Immunol., 2005: 23, 275-306).

A number of diseases and disorders are related to abnormalities in TLRs, such as melanoma, non-small cell lung carcinoma, hepatocellular carcinoma, basal cell carcinoma, renal cell carcinoma, myeloma, allergic rhinitis, asthma, chronic obstructive pulmonary disease (COPD), ulcerative colitis, hepatic fibrosis, and viral infections such as HBV, Flaviviridae viruses, HCV, HPV, RSV, SARS, HIV, or influenza. Therefore, the use of a TLR agonist to treat related diseases is very promising.

Since TLR7 and TLR8 are highly homologous, the ligand of TLR7 in most cases is also the ligand of TLR8. TLR8 stimulation mainly induces the production of cytokines such as tumor necrosis factor α (TNF-α) and chemokine. Interferon α is one of the main drugs for treating chronic hepatitis B or hepatitis C, while TNF-α is a pro-inflammatory cytokine, and its over-secretion may cause severe side effects. Therefore, the selectivity for TLR7 and TLR8 is critical for the development of TLR7 agonists for treating virus infective diseases.

There are currently patent applications related to TLR7 agonists, such as WO2005025583, WO2007093901, WO2008011406, WO2009091032, WO2010077613, WO2010133882, WO2011031965 and WO2012080730. However, there is still a need to continue to develop TLR7 agonists that are safer and more therapeutically effective.

In view of the above technical problems, the present invention provides a pharmaceutical compound having a lower onset concentration, better selectivity (selective for TLR7, and no activation effect on TLR8), more effective activation effect and at the same time, due to a weak inhibitory effect on CYP, it is a safer and more effective TLR7 agonist.

SUMMARY OF THE INVENTION

The object of the present invention is to provide a compound of formula (I):

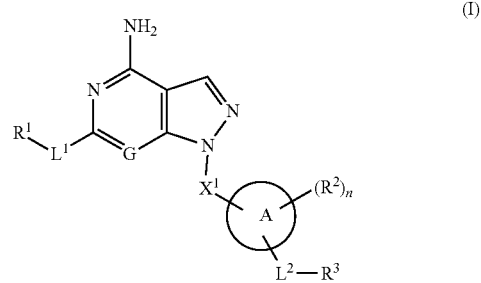

or a tautomer, mesomer, racemate, enantiomer, diastereomer thereof, or mixture thereof, or a pharmaceutically acceptable salt thereof, wherein:

ring A is selected from the group consisting of cycloalkyl, heterocyclyl, aryl and heteroaryl;

G is CH or N;

$X^1$ is alkylene or $S(O)_m$, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;

$L^1$ is selected from the group consisting of —$NR^4$—, —O—, —S—, —C(O)—, —C(O)—$OR^4$, —$S(O)_m$—, —$N(R^4)C(O)$—, —$C(O)N(R^4)$—, —$N(R^4)S(O)_2$—, —$S(O)_2N(R^4)$— and a covalent bond;

$R^1$ is selected from the group consisting of alkyl, alkoxy, haloalkyl, alkenyl, alkynyl, cycloalkyl, heterocyclyl, aryl and heteroaryl, wherein the alkyl, alkenyl, alkynyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$;

each R$^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$;

L$^2$ is alkylene or a covalent bond, wherein the alkylene is optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$;

R$^3$ is selected from the group consisting of haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$, wherein the cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^8$, —C(O)R$^8$, —S(O)$_m$R$^8$, —NR$^9$R$^{10}$ and —C(O)NR$^9$R$^{10}$;

R$^4$ is selected from the group consisting of hydrogen, alkyl, haloalkyl, cycloalkyl, heterocyclyl, aryl and heteroaryl;

R$^5$ is selected from the group consisting of hydrogen, alkyl, haloalkyl, amino, hydroxy, cycloalkyl, heterocyclyl, aryl and heteroaryl;

R$^6$ and R$^7$ are identical or different and are each independently selected from the group consisting of hydrogen, alkyl, haloalkyl, cycloalkyl, heterocyclyl, aryl, heteroaryl, —C(O)R$^8$, —S(O)$_m$R$^8$ and —C(O)NR$^9$R$^{10}$, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, R$^6$ and R$^7$ together with the nitrogen to which they are attached form a heterocyclyl, wherein the heterocyclyl optionally contains one or two identical or different heteroatoms selected from the group consisting of N, O and S in addition to one nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

R$^8$ is selected from the group consisting of hydrogen, alkyl, haloalkyl, amino, hydroxy, cycloalkyl, heterocyclyl, aryl and heteroaryl;

R$^9$ and R$^{10}$ are identical or different and are each independently selected from the group consisting of hydrogen, alkyl, haloalkyl, amino, hydroxy, cycloalkyl, heterocyclyl, aryl and heteroaryl;

n is 0, 1, 2, 3 or 4; and m is 0, 1 or 2.

In a preferred embodiment of the present invention, in the compound of formula (I), R$^3$ is heterocyclyl, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl.

In a preferred embodiment of the present invention, in the compound of formula (I), R$^3$ is —NR$^6$R$^7$, and R$^6$ and R$^7$ together with the nitrogen to which they are attached form a heterocyclyl, wherein the heterocyclyl optionally contains one or two identical or different heteroatoms selected from the group consisting of N, O and S in addition to one nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl.

In a preferred embodiment of the present invention, in the compound of formula (I), the ring A is selected from the group consisting of phenyl and pyridyl.

In a preferred embodiment of the present invention, in the compound of formula (I), the pyridyl is selected from the group consisting of

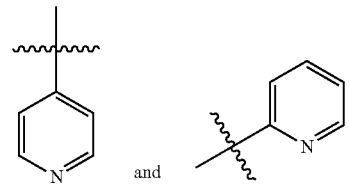

In a preferred embodiment of the present invention, in the compound of formula (I), X$^1$ is alkylene.

In a preferred embodiment of the present invention, the compound of formula (I) is a compound of formula (II):

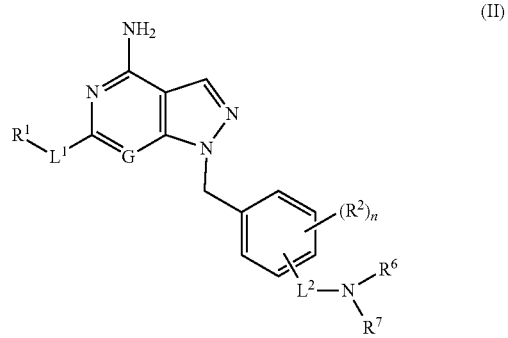

or a tautomer, mesomer, racemate, enantiomer, diastereomer thereof, or mixture thereof, or a pharmaceutically acceptable salt thereof, wherein G L$^1$~L$^2$, R$^1$~R$^2$, R$^6$~R$^7$ and n are as defined in formula (I).

In a preferred embodiment of the present invention, in the compound of formula (I), G is N.

In a preferred embodiment of the present invention, in the compound of formula (I), L$^2$ is alkylene.

In a preferred embodiment of the present invention, the compound of formula (I) is a compound of formula (III):

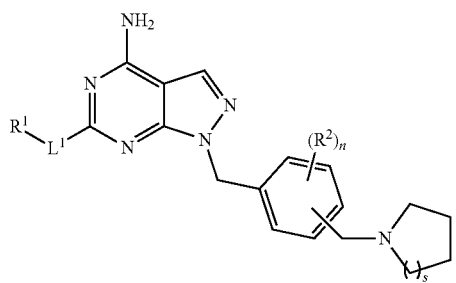

(III)

or a tautomer, mesomer, racemate, enantiomer, diastereomer thereof, or mixture thereof, or a pharmaceutically acceptable salt thereof, wherein:

s is 0, 1 or 2;

$L^1$, $R^1 \sim R^2$ and n are as defined in formula (I).

In a preferred embodiment of the present invention, in the compound of formula (I), $L^1$ is selected from the group consisting of —O—, —$NR^4$—, —C(O)— and —C(O)N($R^4$)—, and $R^4$ is hydrogen or alkyl.

In a preferred embodiment of the present invention, in the compound of formula (I), $R^1$ is alkyl optionally substituted by one or more alkoxy.

In a preferred embodiment of the present invention, in the compound of formula (I), each $R^2$ is identical or different and each is independently hydrogen or halogen.

Typical compounds of the present invention include, but are not limited to:

| Example No. | Structure and name of the compound |
|---|---|
| 1 | 6-Butoxy-1-(4-(pyrrolidin-1-ylmethyl)benzyl)-1H-pyrazolo[3,4-d]pyrimidin-4-amine |
| 2 | 1-(4-(Azetidin-1-ylmethyl)benzyl)-6-butoxy-1H-pyrazolo[3,4-d]pyrimidin-4-amine |
| 3 | 6-Butoxy-1-(4-(piperidin-1-ylmethyl)benzyl)-1H-pyrazolo[3,4-d]pyrimidin-4-amine |
| 4 | 6-Butoxy-1-(3-(pyrrolidin-1-ylmethyl)benzyl)-1H-pyrazolo[3,4-d]pyrimidin-4-amine |
| 5 | 1-(3-(Azetidin-1-ylmethyl)benzyl)-6-butoxy-1H-pyrazolo[3,4-d]pyrimidin-4-amine |
| 6 | 6-Butoxy-1-(3-(piperidin-1-ylmethyl)benzyl)-1H-pyrazolo[3,4-d]pyrimidin-4-amine |
| 7 | 6-(2-Methoxyethoxy)-1-(4-(pyrrolidin-1-ylmethyl)benzyl)-1H-pyrazolo[3,4-d]pyrimidin-4-amine |

| Example No. | Structure and name of the compound |
|---|---|
| 8 | 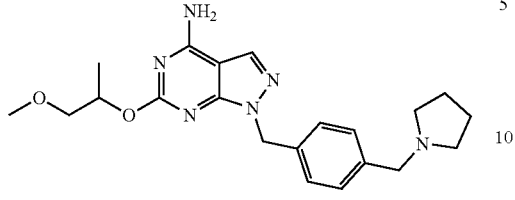<br>8<br>6-((1-Methoxypropan-2-yl)oxy)-1-(4-(pyrrolidin-1-ylmethyl)benzyl)-1H-pyrazolo[3,4-d]pyrimidin-4-amine |
| 9 | 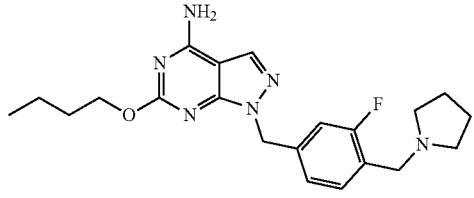 [SMILES: CCCCOc1nc(N)c2cnn(Cc3ccc(CN4CCCC4)c(F)c3)c2n1]<br>9<br>6-Butoxy-1-(3-fluoro-4-(pyrrolidin-1-ylmethyl)benzyl)-1H-pyrazolo[3,4-d]pyrimidin-4-amine |
| 10 | 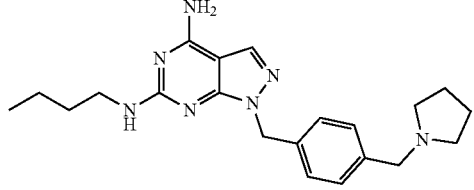 [SMILES: CCCCNc1nc(N)c2cnn(Cc3ccc(CN4CCCC4)cc3)c2n1]<br>10<br>$N^6$-Butyl-1-(4-(pyrrolidin-1-ylmethyl)benzyl)-1H-pyrazolo[3,4-d]pyrimidine-4,6-diamine |
| 11 | 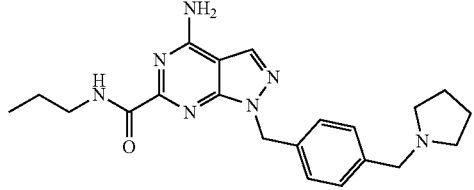 [SMILES: CCCNC(=O)c1nc(N)c2cnn(Cc3ccc(CN4CCCC4)cc3)c2n1]<br>11<br>4-Amino-N-propyl-1-(4-(pyrrolidin-1-ylmethyl)benzyl)-1H-pyrazolo[3,4-d]pyrimidine-6-carboxamide |
| 12 | 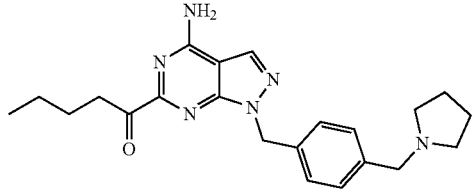 [SMILES: CCCCC(=O)c1nc(N)c2cnn(Cc3ccc(CN4CCCC4)cc3)c2n1]<br>12<br>1-(4-Amino-1-(4-(pyrrolidin-1-ylmethyl)benzyl)-1H-pyrazolo[3,4-d]pyrimidin-6-yl)pentan-1-one | or a tautomer, mesomer, racemate, enantiomer, diastereomer thereof, or mixture thereof, or a pharmaceutically acceptable salt thereof.

In another aspect, the present invention relates to a compound of formula (I-C):

(I-C)

or a tautomer, mesomer, racemate, enantiomer, diastereomer thereof, or mixture thereof, or a pharmaceutically acceptable salt thereof, wherein:

W is an amino protecting group, preferably tert-butoxycarbonyl, acetyl, benzyl, allyl or p-methoxybenzyl;

X is halogen, preferably chlorine;

ring A, G, $X^1$, $L^2$, $R^2 \sim R^3$ and n are as defined in formula (I).

The compounds of formula (I-C) include, but are not limited to:

| Example No. | Structure and name of the compound |
|---|---|
| 1e | 6-Chloro-N-(4-methoxybenzyl)-1-(4-(pyrrolidin-1-ylmethyl)benzyl)-1H-pyrazolo[3,4-d]pyrimidin-4-amine 1e |
| 2f | 1-(4-(Azetidin-1-ylmethyl)benzyl)-6-chloro-N-(4-methoxybenzyl)-1H-pyrazolo[3,4-d]pyrimidin-4-amine 2f |
| 3c | 6-Chloro-N-(4-methoxybenzyl)-1-(4-(piperidin-1-ylmethyl)benzyl)-1H-pyrazolo[3,4-d]pyrimidin-4-amine 3c |

| Example No. | Structure and name of the compound |
|---|---|
| 4b | 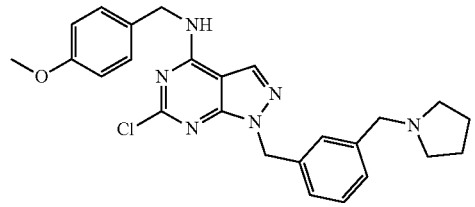 [SMILES: COc1ccc(CNc2nc(Cl)nc3c2cnn3Cc2cccc(CN3CCCC3)c2)cc1]<br>4b<br>6-Chloro-N-(3-methoxybenzyl)-1-(4-(pyrrolidin-1-ylmethyl)benzyl)-1H-pyrazolo[3,4-d]pyrimidin-4-amine 4b |
| 5e | 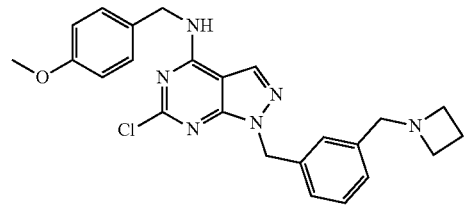 [SMILES: COc1ccc(CNc2nc(Cl)nc3c2cnn3Cc2cccc(CN3CCC3)c2)cc1]<br>5e<br>1-(3-(Azetidin-1-ylmethyl)benzyl)-6-chloro-N-(4-methoxybenzyl)-1H-pyrazolo[3,4-d]pyrimidin-4-amine 5e |
| 6c | 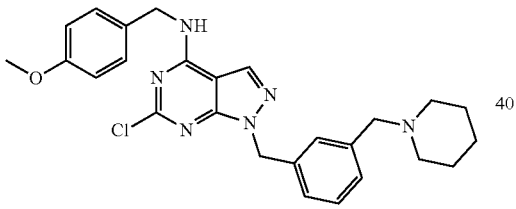<br>6c<br>6-Chloro-N-(3-methoxybenzyl)-1-(4-(piperidin-1-ylmethyl)benzyl)-1H-pyrazolo[3,4-d]pyrimidin-4-amine 6c |
| 9f | 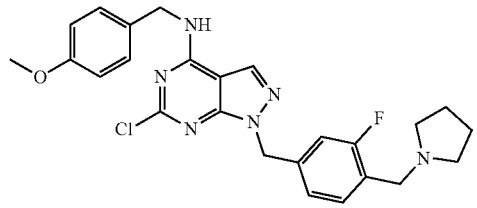 [SMILES: COc1ccc(CNc2nc(Cl)nc3c2cnn3Cc2ccc(CN3CCCC3)c(F)c2)cc1]<br>9f<br>6-Chloro-1-(3-fluoro-4-(pyrrolidin-1-ylmethyl)benzyl)-N-(4-methoxybenzyl)-1H-pyrazolo[3,4-d]pyrimidin-4-amine 9f |

In another aspect, the present invention relates to a compound of formula (I-E):

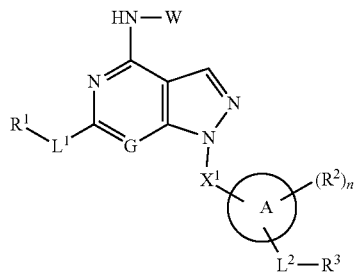

(I-E)

or a tautomer, mesomer, racemate, enantiomer, diastereomer thereof, or mixture thereof, or a pharmaceutically acceptable salt thereof, wherein:

W is an amino protecting group, preferably tert-butoxycarbonyl, acetyl, benzyl, allyl or p-methoxybenzyl;

ring A, G, $X^1$, $L^1$~$L^2$, $R^1$~$R^3$ and n are as defined in formula (I).

The compounds of formula (I-E) include, but are not limited to:

| Example No. | Structure and name of the compound |
|---|---|
| 1f | 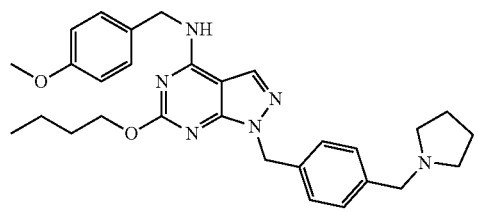 [SMILES: CCCCOc1nc(NCc2ccc(OC)cc2)c2cnn(Cc3ccc(CN4CCCC4)cc3)c2n1]<br>1f<br>6-Butoxy-N-(4-methoxybenzyl)-1-(4-(pyrrolidin-1-ylmethyl)benzyl)-1H-pyrazolo[3,4-d]pyrimidin-4-amine 1f |
| 2g | 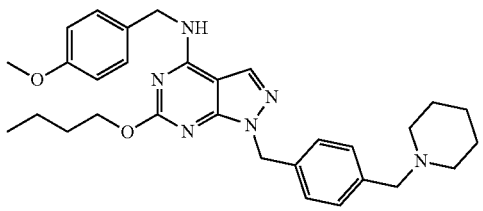 [SMILES: CCCCOc1nc(NCc2ccc(OC)cc2)c2cnn(Cc3ccc(CN4CCCCC4)cc3)c2n1]<br>2g<br>1-(4-(Azetidin-1-ylmethyl)benzyl)-6-butoxy-N-(4-methoxybenzyl)-1H-pyrazolo[3,4-d]pyrimidin-4-amine 2g |
| 3d | 3d<br>6-Butoxy-N-(4-methoxybenzyl)-1-(4-(piperidin-1-ylmethyl)benzyl)-1H-pyrazolo[3,4-d]pyrimidin-4-amine 3d |

-continued

| Example No. | Structure and name of the compound |
|---|---|
| 4c | 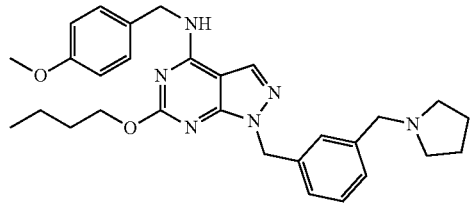 [SMILES: CCCCOc1nc(NCc2ccc(OC)cc2)c2cnn(Cc3cccc(CN4CCCC4)c3)c2n1]<br>4c<br>6-Butoxy-N-(3-methoxybenzyl)-1-(4-(pyrrolidin-1-ylmethyl) benzyl)-1H-pyrazolo[3,4-d]pyrimidin-4-amine 4c |
| 5f | 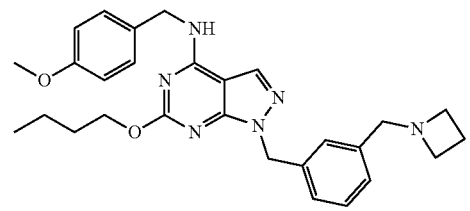 [SMILES: CCCCOc1nc(NCc2ccc(OC)cc2)c2cnn(Cc3cccc(CN4CCC4)c3)c2n1]<br>5f<br>1-(3-(Azetidin-1-ylmethyl)benzyl)-6-butoxy-N-(4-methoxybenzyl)-1H-pyrazolo[3,4-d]pyrimidin-4-amine 5f |
| 6d | 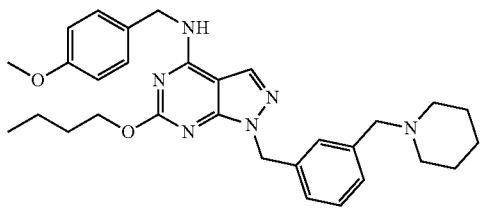 [SMILES: CCCCOc1nc(NCc2ccc(OC)cc2)c2cnn(Cc3cccc(CN4CCCCC4)c3)c2n1]<br>6d<br>6-Butoxy-N-(3-methoxybenzyl)-1-(4-(piperidin-1-ylmethyl) benzyl)-1H-pyrazolo[3,4-d]pyrimidin-4-amine 6d |
| 7a | 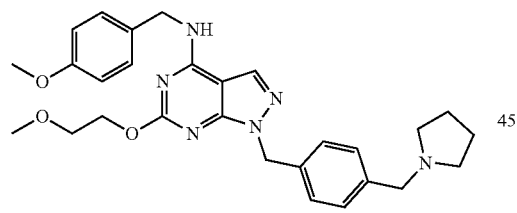<br>7a<br>N-(4-Methoxybenzyl)-6-(2-methoxyethoxy)-1-(4-(pyrrolidin-1-ylmethyl)benzyl)-1H-pyrazolo[3,4-d]pyrimidin-4-amine 7a |
| 8a | 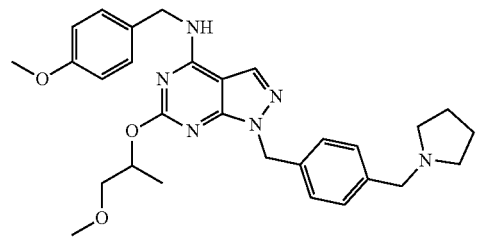 [SMILES: COCC(C)Oc1nc(NCc2ccc(OC)cc2)c2cnn(Cc3ccc(CN4CCCC4)cc3)c2n1]<br>8a<br>N-(4-Methoxybenzyl)-6-((1-methoxypropan-2-yl)oxy)-1-(4-(pyrrolidin-1-ylmethyl)benzyl)-1H-pyrazolo[3,4-d] pyrimidin-4-amine 8a |

-continued

| Example No. | Structure and name of the compound |
|---|---|
| 9g | 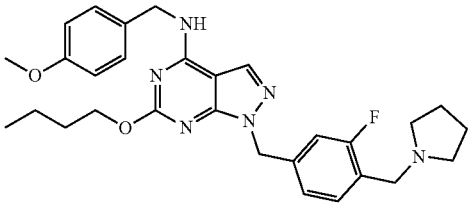 [SMILES: CCCCOc1nc(NCc2ccc(OC)cc2)c2cnn(Cc3ccc(CN4CCCC4)c(F)c3)c2n1]<br>9g<br>6-Butoxy-1-(3-fluoro-4-(pyrrolidin-1-ylmethyl)benzyl)-N-(4-methoxybenzyl)-1H-pyrazolo[3,4-d]pyrimidin-4-amine 9g |
| 10a | 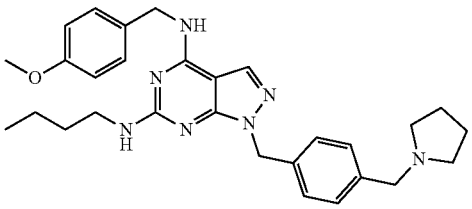 [SMILES: CCCCNc1nc(NCc2ccc(OC)cc2)c2cnn(Cc3ccc(CN4CCCC4)cc3)c2n1]<br>10a<br>$N^6$-Butyl-$N^4$-(4-methoxybenzyl)-1-(4-(pyrrolidin-1-ylmethyl)benzyl)-1H-pyrazolo[3,4-d]pyrimidine-4,6-diamine 10a |
| 11a | 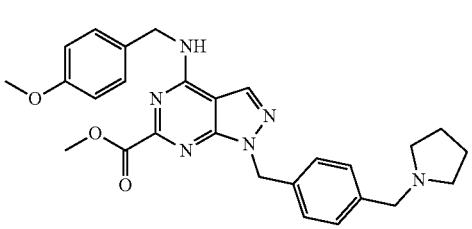 [SMILES: COC(=O)c1nc(NCc2ccc(OC)cc2)c2cnn(Cc3ccc(CN4CCCC4)cc3)c2n1]<br>11a<br>Methyl 4-((4-methoxybenzyl)amino)-1-(4-(pyrrolidin-1-ylmethyl)benzyl)-1H-pyrazolo[3,4-d]pyrimidine-6-carboxylate 11a |
| 11b | 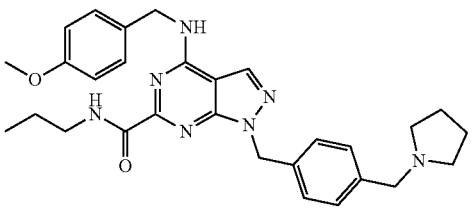 [SMILES: CCCNC(=O)c1nc(NCc2ccc(OC)cc2)c2cnn(Cc3ccc(CN4CCCC4)cc3)c2n1]<br>11b<br>4-((4-Methoxybenzyl)amino)-N-propyl-1-(4-(pyrrolidin-1-ylmethyl)benzyl)-1H-pyrazolo[3,4-d]pyrimidine-6-carboxamide 11b |
| 12b | 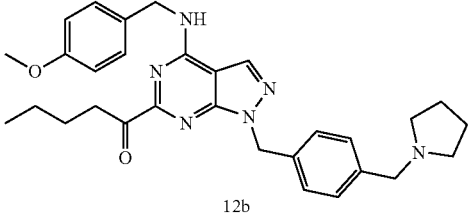<br>12b<br>1-(4-((4-Methoxybenzyl)amino)-1-(4-(pyrrolidin-1-ylmethyl)benzyl)-1H-pyrazolo[3,4-d]pyrimidin-6-yl) pentan-1-one 12b |

In another aspect, the present invention relates to a method for preparing the compound of formula (I-E), comprising a step of:

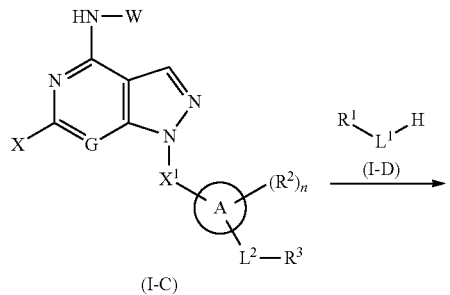

subjecting a compound of formula (I-C) and a compound of formula (I-D) to a nucleophilic substitution reaction under an alkaline condition to obtain the compound of formula (I-E);

wherein:

W is an amino protecting group, preferably tert-butoxycarbonyl, acetyl, benzyl, allyl or p-methoxybenzyl;

X is halogen, preferably chlorine;

ring A, G, $L^1$~$L^2$, $X^1$, $R^1$~$R^3$ and n are as defined in formula (I-E).

In another aspect, the present invention relates to a method for preparing the compound of formula (I), comprising a step of:

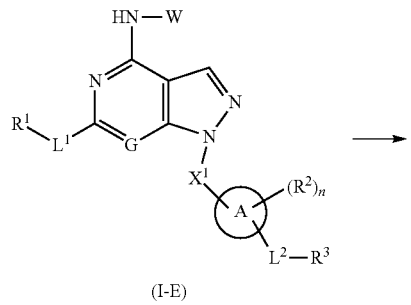

removing the protecting group of the compound of formula (I-E) under an acidic condition to obtain the compound of formula (I);

wherein:

W is an amino protecting group, preferably tert-butoxycarbonyl, acetyl, benzyl, allyl or p-methoxybenzyl;

ring A, G, $L^1$~$L^2$, $X^1$, $R^1$~$R^3$ and n are as defined in formula (I).

In another aspect, the present invention relates to a compound of formula (II-B):

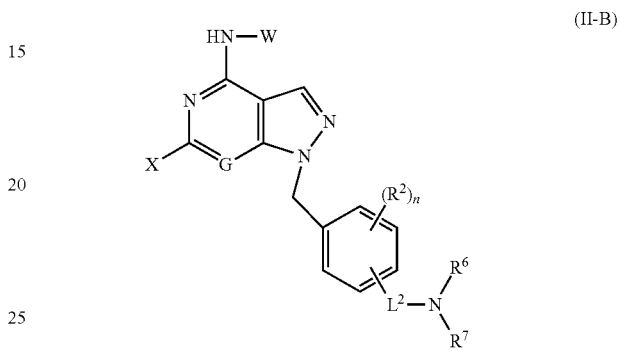

or a tautomer, mesomer, racemate, enantiomer, diastereomer thereof, or mixture thereof, or a pharmaceutically acceptable salt thereof, wherein:

W is an amino protecting group, preferably tert-butoxycarbonyl, acetyl, benzyl, allyl or p-methoxybenzyl;

X is halogen, preferably chlorine;

G, $L^2$, $R^2$, $R^6$~$R^7$ and n are as defined in formula (II).

In another aspect, the present invention relates to a compound of formula (II-C):

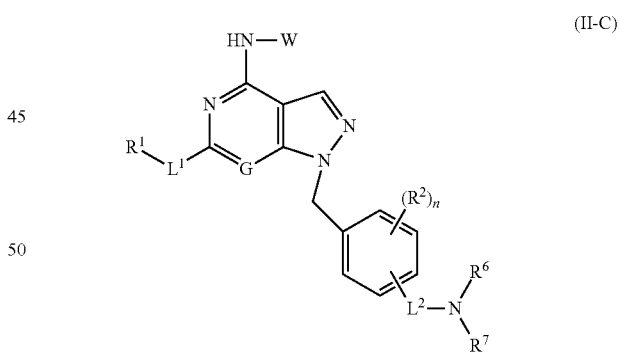

or a tautomer, mesomer, racemate, enantiomer, diastereomer thereof, or mixture thereof, or a pharmaceutically acceptable salt thereof, wherein:

W is an amino protecting group, preferably tert-butoxycarbonyl, acetyl, benzyl, allyl or p-methoxybenzyl;

G, $L^1$~$L^2$, $R^1$~$R^2$, $R^6$~$R^7$ and n are as defined in formula (II).

In another aspect, the present invention relates to a method for preparing the compound of formula (II-C), comprising a step of:

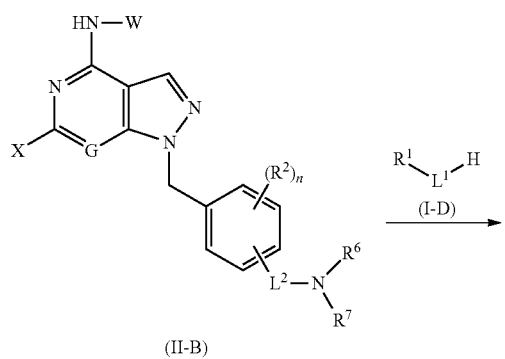

(II-B)

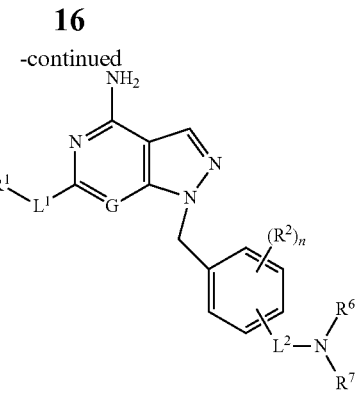

(II)

removing the protecting group of the compound of formula (II-C) under an acidic condition to obtain the compound of formula (II);

wherein:

W is an amino protecting group, preferably tert-butoxycarbonyl, acetyl, benzyl, allyl or p-methoxybenzyl;

G, $L^1\sim L^2$, $R^1\sim R^2$, $R^6\sim R^7$ and n are as defined in formula (II).

In another aspect, the present invention relates to a method for preparing the compound of formula (III), comprising a step of:

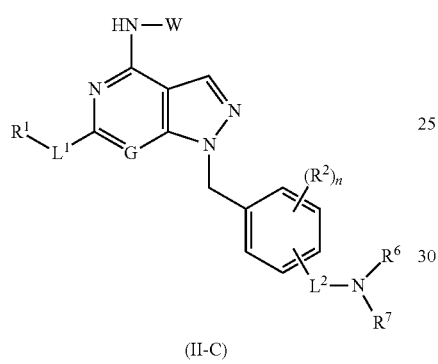

(II-C)

subjecting a compound of formula (II-B) and a compound of formula (I-D) to a nucleophilic substitution reaction under an alkaline condition to obtain the compound of formula (II-C);

wherein:

W is an amino protecting group, preferably tert-butoxycarbonyl, acetyl, benzyl, allyl or p-methoxybenzyl;

X is halogen, preferably chlorine;

G, $L^1\sim L^2$, $R^1\sim R^2$, $R^6\sim R^7$ and n are as defined in formula (II).

In another aspect, the present invention relates to a method for preparing the compound of formula (II), comprising a step of:

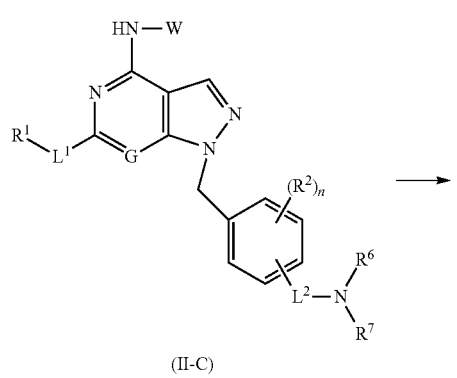

(II-C)

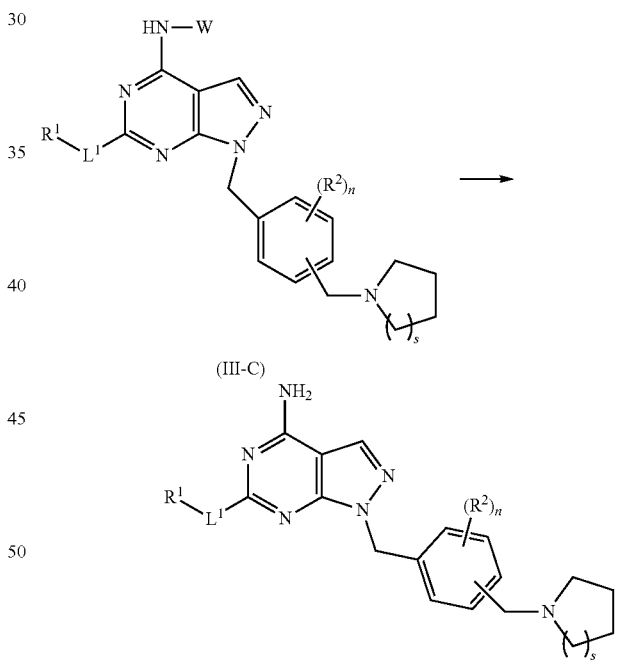

(III-C)

(III)

removing the protecting group of the compound of formula (III-C) under an acidic condition to obtain the compound of formula (III);

wherein:

W is an amino protecting group, preferably tert-butoxycarbonyl, acetyl, benzyl, allyl or p-methoxybenzyl;

$L^1$, $R^1\sim R^2$, s and n are as defined in formula (III).

In another aspect, the present invention relates to a pharmaceutical composition, comprising a therapeutically effective amount of the compound of formula (I), or a tautomer, mesomer, racemate, enantiomer, diastereomer thereof, or mixture thereof, or a pharmaceutically acceptable salt thereof, and one or more pharmaceutically acceptable carriers, diluents or excipients.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for activating TLR7.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating an infection caused by a virus selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral disarrhea virus, Zika virus, HIV, HBV, HCV, HPV, RSV, SARS and influenza virus.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating or preventing melanoma, non-small cell lung carcinoma, hepatocellular carcinoma, basal cell carcinoma, renal cell carcinoma, myeloma, allergic rhinitis, asthma, COPD, ulcerative colitis and hepatic fibrosis.

The present invention further relates to the compound of formula (I), or a tautomer, mesomer, racemate, enantiomer, diastereomer thereof, or mixture thereof, or a pharmaceutically acceptable salt thereof, or a pharmaceutical composition comprising the same, for use as a medicament.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in activating TLR7.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating an infection caused by a virus selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral disarrhea virus, Zika virus, HIV, HBV, HCV, HPV, RSV, SARS and influenza virus.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating or preventing melanoma, non-small cell lung carcinoma, hepatocellular carcinoma, basal cell carcinoma, renal cell carcinoma, myeloma, allergic rhinitis, asthma, COPD, ulcerative colitis or hepatic fibrosis.

The present invention further relates to a method for activating TLR7, comprising administering to a patient in need thereof a therapeutically effective amount of the compound of formula (I) of the present invention, or a tautomer, mesomer, racemate, enantiomer, diastereomer thereof, or mixture thereof, or a pharmaceutically acceptable salt thereof, or the pharmaceutical composition comprising the same.

The present invention further relates to a method for treating an infection caused by a virus selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral disarrhea virus, Zika virus, HIV, HBV, HCV, HPV, RSV, SARS and influenza virus, comprising administering to a patient in need thereof a therapeutically effective amount of the compound of formula (I) of the present invention, or a tautomer, mesomer, racemate, enantiomer, diastereomer thereof, or mixture thereof, or a pharmaceutically acceptable salt thereof, or the pharmaceutical composition comprising the same.

The present invention further relates to a method for treating or preventing melanoma, non-small cell lung carcinoma, hepatocellular carcinoma, basal cell carcinoma, renal cell carcinoma, myeloma, allergic rhinitis, asthma, COPD, ulcerative colitis and hepatic fibrosis, comprising administering to a patient in need thereof a therapeutically effective amount of the compound of formula (I) of the present invention, or a tautomer, mesomer, racemate, enantiomer, diastereomer thereof, or mixture thereof, or a pharmaceutically acceptable salt thereof, or the pharmaceutical composition comprising the same.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical composition. Such composition can contain one or more ingredients selected from the group consisting of sweetening agents, flavoring agents, coloring agents and preservatives, in order to provide a pleasing and palatable pharmaceutical preparation. Tablets contain the active ingredient in admixture with nontoxic pharmaceutically acceptable excipients suitable for the manufacture of tablets.

An aqueous suspension contains the active ingredient in admixture with excipients suitable for the manufacture of an aqueous suspension. The aqueous suspension can also contain one or more preservative such as ethylparaben or n-propylparaben, one or more coloring agents, one or more flavoring agents, and one or sweetening agents.

An oil suspension can be formulated by suspending the active ingredient in a vegetable oil. The oil suspension can contain a thickener. The aforementioned sweetening agents and flavoring agents can be added to provide a palatable formulation.

The active ingredient in admixture with the dispersants or wetting agents, suspending agent or one or more preservatives can be prepared as a dispersible powder or granule suitable for the preparation of an aqueous suspension by adding water.

Suitable dispersants or wetting agents and suspending agents are exemplified by those already mentioned above. Additional excipients, such as sweetening agents, flavoring agents and coloring agents, can also be added. These compositions can be preserved by adding an antioxidant such as ascorbic acid.

The pharmaceutical composition of the present invention can also be in the form of an oil-in-water emulsion.

The pharmaceutical composition can be in the form of sterile injectable aqueous solution. The acceptable vehicles and solvents that can be employed are water, Ringer's solution and isotonic sodium chloride solution. The sterile injectable formulation can be a sterile injectable oil-in-water micro-emulsion in which the active ingredient is dissolved in the oil phase. For example, the active ingredient is dissolved in a mixture of soybean oil and lecithin, the oil solution is then added into a mixture of water and glycerol and processed to form a micro-emulsion. The injectable solution or micro-emulsion can be injected into a patient's bloodstream by local bolus injection. Alternatively, it can be advantageous to administer the solution and micro-emulsion in such a way as to maintain a constant circulating concentration of the compound of the present invention. In order to maintain such a constant concentration, a continuous intravenous delivery device can be utilized. An example of such a device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can readily be used as a solvent or suspending medium.

The compound of the present invention can be administered in the form of a suppository for rectal administration. These pharmaceutical compositions can be prepared by mixing the drug with a suitable non-irritating excipient that is solid at normal temperature, but liquid in the rectum, thereby melting in the rectum to release the drug. Such materials include cocoa butter, glycerin gelatin, hydrogenated vegetable oils, mixtures of polyethylene glycols with various molecular weights and fatty acid esters of polyethylene glycols.

It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by conventional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —OR$^5$, —C(O)R$^5$, —S(O)$_m$R$^5$, —NR$^6$R$^7$ and —C(O)NR$^6$R$^7$.

The term "alkylene" refers to a saturated linear or branched aliphatic hydrocarbon group having two residues derived from the removal of two hydrogen atoms from the same carbon atom or two different carbon atoms of the parent alkane. The linear or branched alkylene has 1 to 20 carbon atoms, preferably 1 to 12 carbon atoms, and more preferably 1 to 6 carbon atoms. Non-limiting examples of alkylene groups include, but are not limited to, methylene (—CH$_2$—), 1,1-ethylene (—CH(CH$_3$)—), 1,2-ethylene (—CH$_2$CH$_2$)—, 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like. The alkylene group can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —OR$^5$, —C(O)R$^5$, —S(O)$_m$R$^5$, —NR$^6$R$^7$ and —C(O)NR$^6$R$^7$.

The term "alkenyl" refers to a hydrocarbon group formed by the removal of one or more hydrogen atoms in an olefin molecule. The alkenyl group can be substituted or unsubstituted. When substituted, the substituent group(s) is preferably one or more groups independently selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$.

The term "alkynyl" refers to a hydrocarbon group containing a carbon-carbon triple bond in the molecule. The alkynyl group can be substituted or unsubstituted. When substituted, the substituent group(s) is preferably one or more groups independently selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —OR⁵, —C(O)R⁵, —S(O)ₘR⁵, —NR⁶R⁷ and —C(O)NR⁶R⁷.

The term "cycloalkyl" refers to a saturated or partially unsaturated monocyclic or polycyclic hydrocarbon group having 3 to 20 carbon atoms, preferably 3 to 12 carbon atoms, preferably 3 to 10 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

The term "amino protecting group" refers to a group which prevents an amino group from reaction when other parts of the molecular are subject to a reaction, and can be easily removed. Non-limiting examples include tert-butoxycarbonyl, acetyl, benzyl, allyl and p-methoxybenzyl and the like. These groups can be optionally substituted by one to three substituent groups selected from the group consisting of halogen, alkoxy and nitro. The amino protecting group is preferably p-methoxybenzyl.

The term "heterocyclyl" refers to a 3 to 20 membered saturated or partially unsaturated monocyclic or polycyclic hydrocarbon substituent group, wherein one or more ring atoms are heteroatoms selected from the group consisting of N, O, and S(O)ₘ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, more preferably 3 to 10 ring atoms wherein 1 to 4 atoms are heteroatoms, and more preferably 5 to 6 ring atoms wherein 1 to 3 atoms are heteroatoms. Non-limiting examples of monocyclic heterocyclyl include pyrrolidinyl, tetrahydropyranyl, 1,2,3,6-tetrahydropyridyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The ring of heterocyclyl can be fused to the ring of aryl, heteroaryl or cycloalkyl, wherein the ring bound to the parent structure is heterocyclyl. Non-limiting examples include:

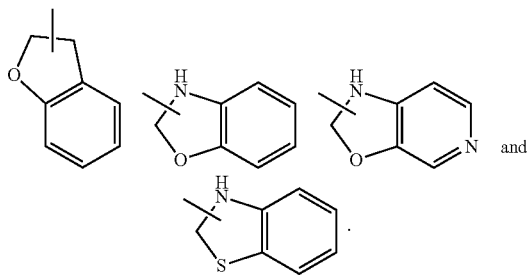

The heterocyclyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —OR, —C(O)R⁵, —S(O)ₘR⁵, —NR⁶R⁷ and —C(O)NR⁶R⁷.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples include:

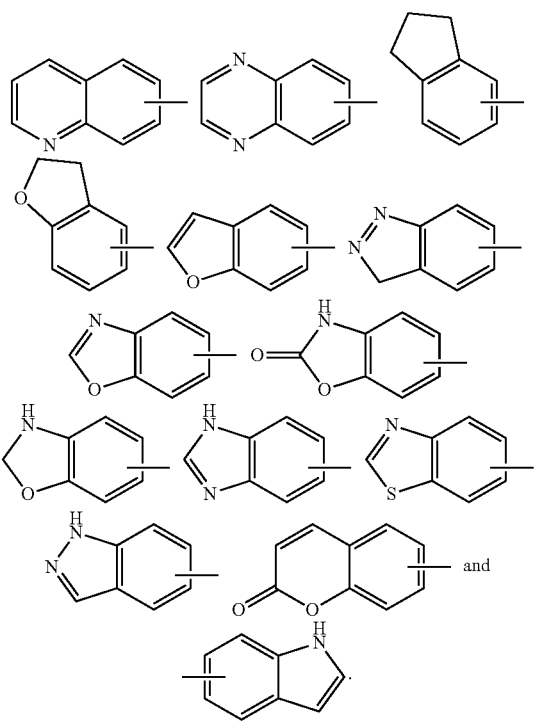

The aryl can be substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR⁵, —C(O)R⁵, —S(O)ₘ R⁵, —NR⁶R⁷ and —C(O)NR⁶R⁷.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, pyridazinyl, imidazolyl, pyrazolyl, tetrazolyl, and the like. The ring of heteroaryl can be fused to the ring of aryl, heterocyclyl or cycloalkyl, wherein the ring bound to the parent structure is heteroaryl ring. Non-limiting examples include:

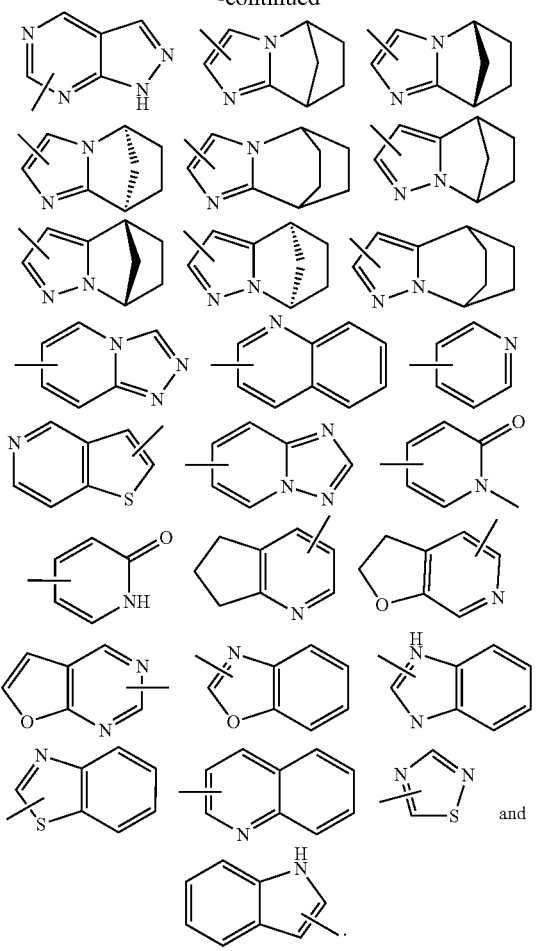

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR$^5$, —C(O)R$^5$, —S(O)$_m$R$^5$, —NR$^6$R$^7$ and —C(O)NR$^6$R$^7$.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of halogen, alkyl, alkoxy, haloalkyl, hydroxy, hydroxyalkyl, cyano, amino, nitro, cycloalkyl, heterocyclyl, aryl and heteroaryl.

The term "haloalkyl" refers to an alkyl group substituted by one or more halogens, wherein the alkyl is as defined above. The term "hydroxy" refers to an —OH group.

The term "hydroxyalkyl" refers to an alkyl group substituted by hydroxy(s), wherein the alkyl is as defined above.

The term "halogen" refers to fluorine, chlorine, bromine or iodine.

The term "amino" refers to a —NH$_2$ group.
The term "cyano" refers to a —CN group.
The term "nitro" refers to a —NO$_2$ group.
The term "oxo" refers to an ═O group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

m and R$^5$ to R$^7$ are as defined in the compound of formula (I).

Synthesis Method of the Compound of the Present Invention

In order to achieve the object of the present invention, the present invention employs the following technical solutions:

Scheme I A method for preparing the compound of formula (I) of the present invention or a tautomer, mesomer, racemate, enantiomer, diastereomer thereof, or mixture thereof, or a pharmaceutically acceptable salt thereof, comprises the following steps of

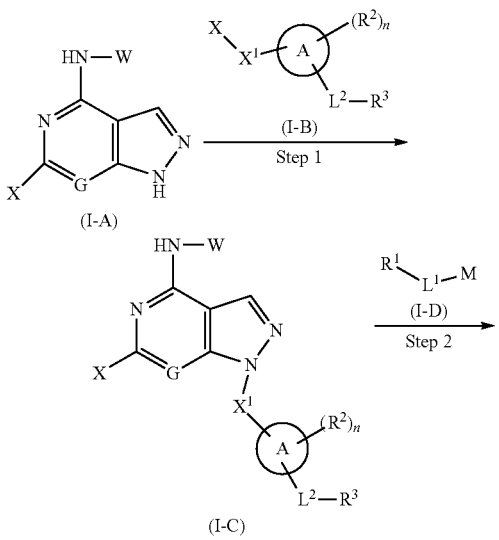

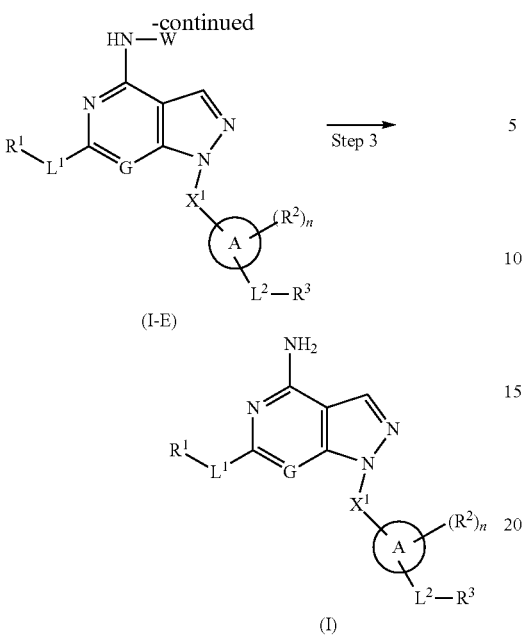

(I-E)

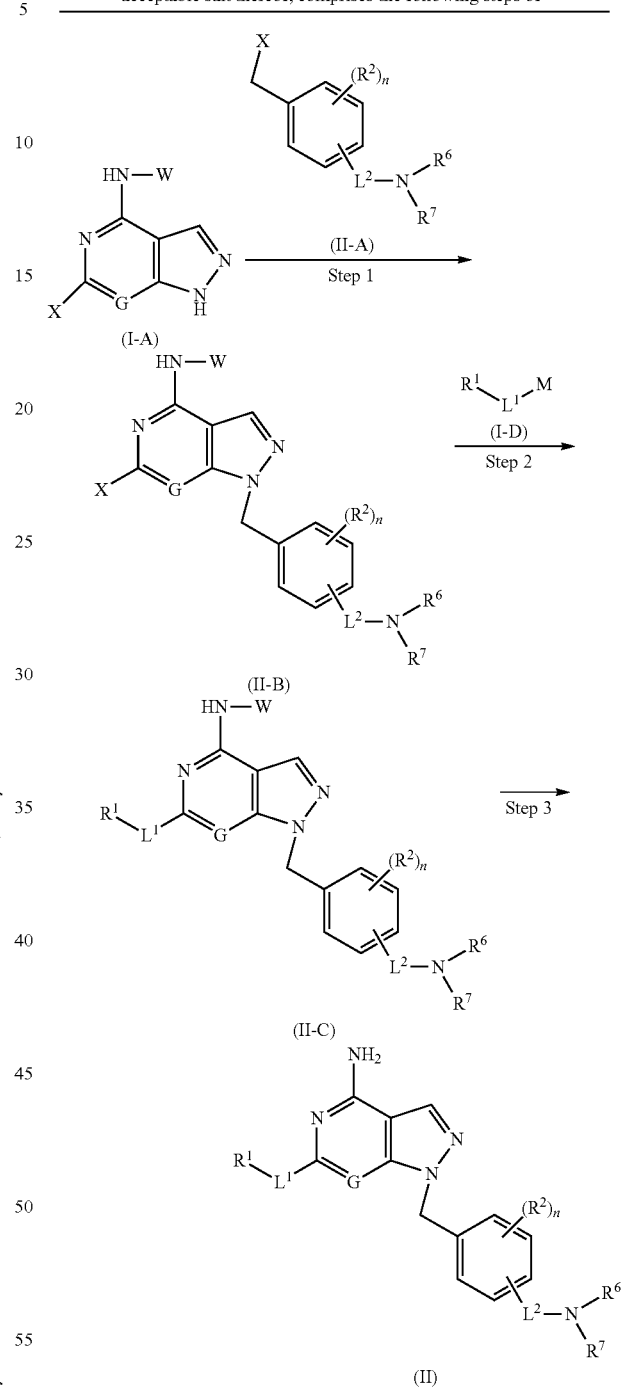

in the first step, a compound of formula (I-A) and a compound of formula (I-B) are subjected to a nucleophilic substitution reaction under an alkaline condition to obtain a compound of formula (I-C);

in the second step, the compound of formula (I-C) and a compound of formula (I-D) are subjected to a nucleophilic substitution reaction under an alkaline condition to obtain a compound of formula (I-E);

in the third step, the protecting group of the compound of formula (I-E) is removed under an acidic condition to obtain the compound of formula (I);

wherein:

M is hydrogen or a metal ion, wherein the metal ion is preferably sodium ion;

W is an amino protecting group, preferably tert-butoxycarbonyl, acetyl, benzyl, allyl or p-methoxybenzyl;

X is halogen, preferably chlorine;

ring A, G $L^1 \sim L^2$, $X^1$, $R^1 \sim R^3$ and n are as defined in formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The reagent that provides an acidic condition includes, but is not limited to, hydrogen chloride, a solution of hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, Me$_3$SiCl, and TMSOTf.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, water and N,N-dimethylformamide.

Scheme II A method for preparing the compound of formula (II) of the present invention or a tautomer, mesomer, racemate, enantiomer, diastereomer thereof, or mixture thereof, or a pharmaceutically acceptable salt thereof, comprises the following steps of in the first step, a compound of formula (I-A) and a compound of formula (I-A) are subjected to a nucleophilic substitution reaction under an alkaline condition to obtain a compound of formula (II-B);

in the second step, the compound of formula (I-B) and a compound of formula (I-D) are subjected to a nucleophilic substitution reaction under an alkaline condition to obtain a compound of formula (II-C);

in the third step, the protecting group of the compound of formula (II-C) is removed under an acidic condition to obtain the compound of formula (II);

wherein:

M is hydrogen or a metal ion, wherein the metal ion is preferably sodium ion;

W is an amino protecting group, preferably tert-butoxycarbonyl, acetyl, benzyl, allyl or p-methoxybenzyl;

X is halogen, preferably chlorine;

G, $L^1 \sim L^2$, $R^1 \sim R^2$, $R^6 \sim R^7$ and n are as defined in formula (II).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The reagent that provides an acidic condition includes, but is not limited to, hydrogen chloride, a solution of hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, $Me_3SiCl$, and TMSOTf.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, water and N,N-dimethylformamide.

Scheme III A method for preparing the compound of formula (III) of the present invention or a tautomer, mesomer, racemate, enantiomer, diastereomer thereof, or mixture thereof, or a pharmaceutically acceptable salt thereof, comprises the following steps of

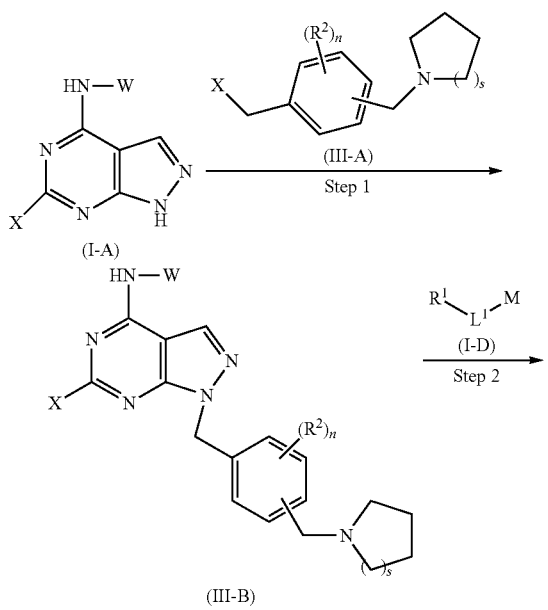

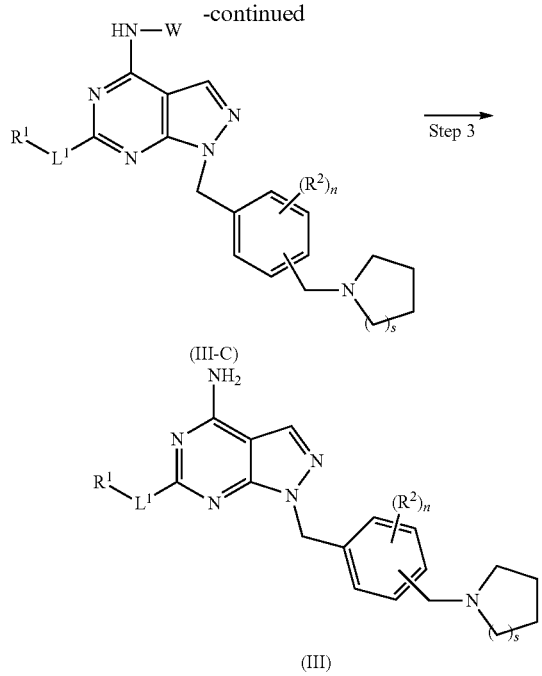

in the first step, a compound of formula (I-A) and a compound of formula (III-A) are subjected to a nucleophilic substitution reaction under an alkaline condition to obtain a compound of formula (III-B);

in the second step, the compound of formula (III-B) and a compound of formula (I-D) are subjected to a nucleophilic substitution reaction under an alkaline condition to obtain a compound of formula (III-C);

in the third step, the protecting group of the compound of formula (III-C) is removed under an acidic condition to obtain the compound of formula (III);

wherein:

M is hydrogen or a metal ion, wherein the metal ion is preferably sodium ion;

W is an amino protecting group, preferably tert-butoxycarbonyl, acetyl, benzyl, allyl or p-methoxybenzyl;

X is halogen, preferably chlorine;

$L^1$, $R^1 \sim R^2$, s and n are as defined in formula (III).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The reagent that provides an acidic condition includes, but is not limited to, hydrogen chloride, a solution of hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, $Me_3SiCl$, and TMSOTf.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, water and N,N-dimethylformamide.

PREFERRED EMBODIMENTS

The present invention will be further described with reference to the following examples, but the examples should not be considered as limiting the scope of the present invention.

EXAMPLES

The structures of the compounds were identified by nuclear magnetic resonance (NMR) and/or mass spectrometry (MS). NMR shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on Agilent HPLC 1200DAD, Agilent HPLC 1200VWD and Waters HPLC e2695-2489 high pressure liquid chromatographs.

Chiral HPLC was determined on an Agilent HPLC 1260 DAD high performance liquid chromatography.

High performance liquid preparation was carried out on Waters 2767, Waters 2767-SQ Detecor2, Shimadzu LC-20AP and Gilson-281 preparative chromatographs.

Chiral preparation was carried out on a Shimadzu LC-20AP preparative chromatography.

CombiFlash rapid preparation instrument used was Combiflash Rf200 (TELEDYNE ISCO).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

The average kinase inhibition rates and $IC_{50}$ values were determined by a NovoStar ELISA (BMG Co., Germany).

The known starting materials of the present invention can be prepared by the known methods in the art, or can be purchased from ABCR GmbH & Co. KQ Acros Organnics, Aldrich Chemical Company, Accela ChemBio Inc., or Dan chemical Company, etc.

Unless otherwise stated, the reactions were carried out under an argon atmosphere or nitrogen atmosphere.

Argon atmosphere or nitrogen atmosphere means that a reaction flask is equipped with an argon or nitrogen balloon (about 1 L).

Hydrogen atmosphere means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, with the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC). The developing solvent used in the reactions, the elution system in column chromatography and the developing solvent system in thin layer chromatography for purification of the compounds included: A: dichloromethane/methanol system, and B: n-hexane/ethyl acetate system. The ratio of the volume of the solvent was adjusted according to the polarity of the compounds, and a small quantity of alkaline reagent such as triethylamine or acidic reagent such as acetic acid can also be added for adjustment.

Example 1

6-Butoxy-1-(4-(pyrrolidin-1-ylmethyl)benzyl)-1H-pyrazolo[3,4-d]pyrimidin-4-amine

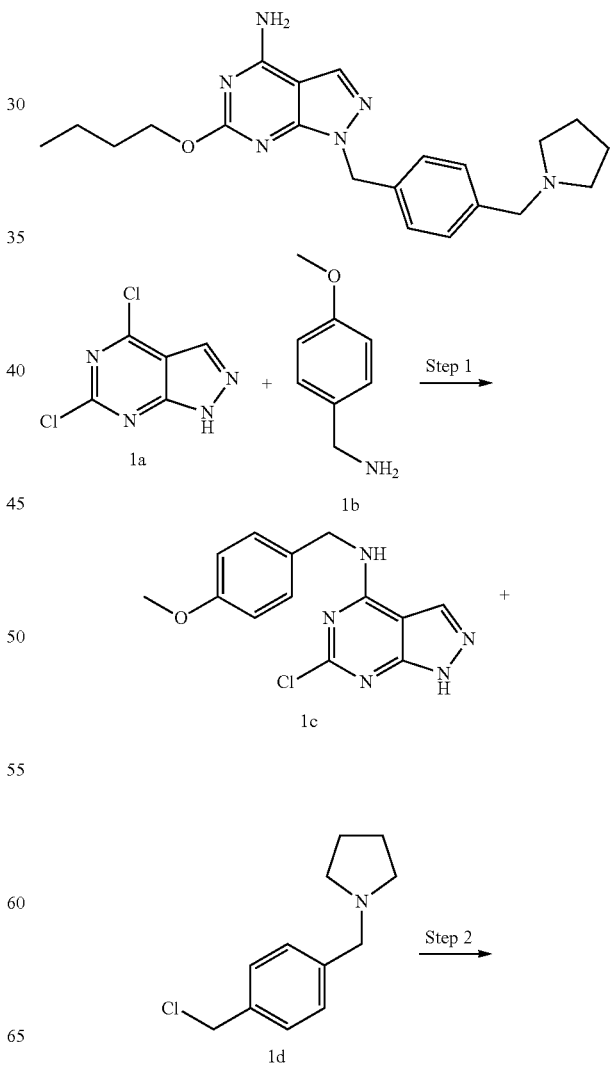

-continued

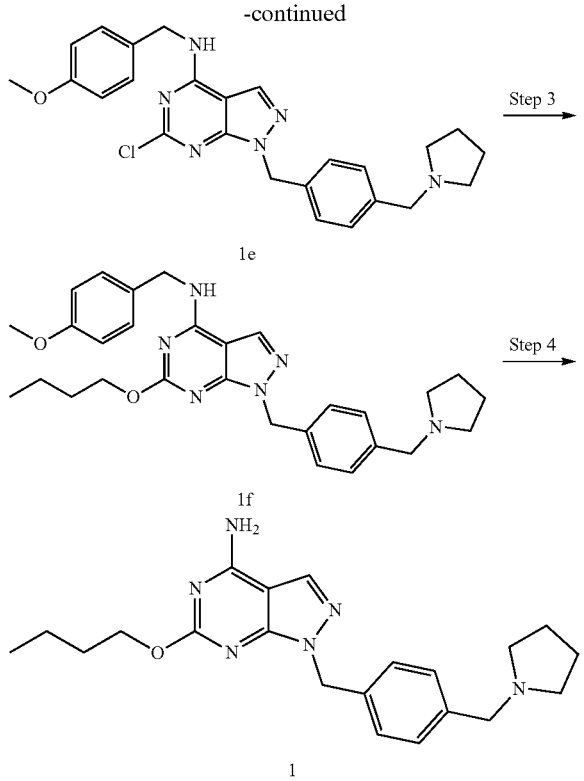

Step 1

6-Chloro-N-(4-methoxybenzyl)-1H-pyrazolo[3,4-d]pyrimidin-4-amine 1c 4,6-Dichloro-1H-pyrazolo[3,4-d]pyrimidine 1a (120 mg, 0.63 mmol), 4-methoxybenzylamine 1b (87.1 mg, 0.63 mmol) and triethylamine (64.13 mg, 0.63 mmol) were dissolved in 2 mL of tetrahydrofuran, and the reaction solution was stirred at room temperature for 1 hour. The reaction was stopped, and the reaction solution was concentrated under reduced pressure. The residue was purified by silica gel column chromatography with elution system A to obtain the title compound 1c (140 mg, yield: 76.1%).

MS m/z (ESI): 290.2 [M+1]

Step 2

6-Chloro-N-(4-methoxybenzyl)-1-(4-(pyrrolidin-1-ylmethyl)benzyl)-1H-pyrazolo[3,4-d]pyrimidin-4-amine 1e Compound 1c (140 mg, 0.48 mmol), 1-(4-(chloromethyl)benzyl)pyrrolidine 1d (101.34 mg, 0.48 mmol, prepared according to the method disclosed in the patent application "WO2002012224") and potassium carbonate (66.79 mg, 0.48 mmol) were dissolved in 2 mL of N,N-dimethylformamide. The reaction was stopped after stirring at room temperature for 16 hours. The reaction solution was concentrated under reduced pressure, and the residue was purified by silica gel column chromatography with elution system A to obtain the title compound 1e (70 mg, yield: 31.3%).

MS m/z (ESI): 463.2 [M+1]

Step 3

6-Butoxy-N-(4-methoxybenzyl)-1-(4-(pyrrolidin-1-ylmethyl)benzyl)-1H-pyrazolo[3,4-d]pyrimidin-4-amine 1f Compound 1e (70 mg, 0.15 mmol), sodium n-butoxide (0.3 mL, 0.60 mmol) and 1 mL of n-butanol were added to a microwave tube successively, heated to 160° C. and stirred for 1.5 hours. The reaction was stopped, and the reaction solution was concentrated under reduced pressure. The residue was purified by silica gel column chromatography with elution system A to obtain the title compound 1f (40 mg, yield: 52.8%).

MS m/z (ESI): 501.2 [M+1]

Step 4

6-Butoxy-1-(4-(pyrrolidin-1-ylmethyl)benzyl)-1H-pyrazolo[3,4-d]pyrimidin-4-amine 1

Compound 1f (40 mg, 0.08 mmol) and 2 mL of trifluoroacetic acid were added to a reaction flask, heated to reflux, and stirred for 24 hours. The reaction was stopped, and the reaction solution was concentrated under reduced pressure and added with 1 mL of ammonia in methanol. The residue was purified by thin layer chromatography with developing solvent system A to obtain the title compound 1 (15 mg, yield: 46.0%).

MS m/z (ESI): 381.2 [M+1]

$^1$H NMR (400 MHz, CD$_3$OD) δ 7.98 (s, 1H), 7.41 (d, 2H), 7.36 (d, 2H), 5.48 (s, 2H), 4.39 (t, 2H), 4.13 (s, 2H), 3.12-3.08 (m, 4H), 2.02-1.98 (m, 4H), 1.80-1.76 (m, 2H), 1.55-1.49 (m, 2H), 1.01 (t, 3H).

Example 2

1-(4-(Azetidin-1-ylmethyl)benzyl)-6-butoxy-1H-pyrazolo[3,4-d]pyrimidin-4-amine 2

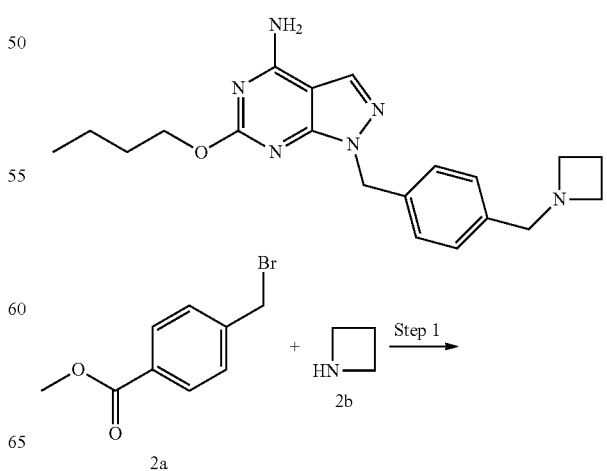

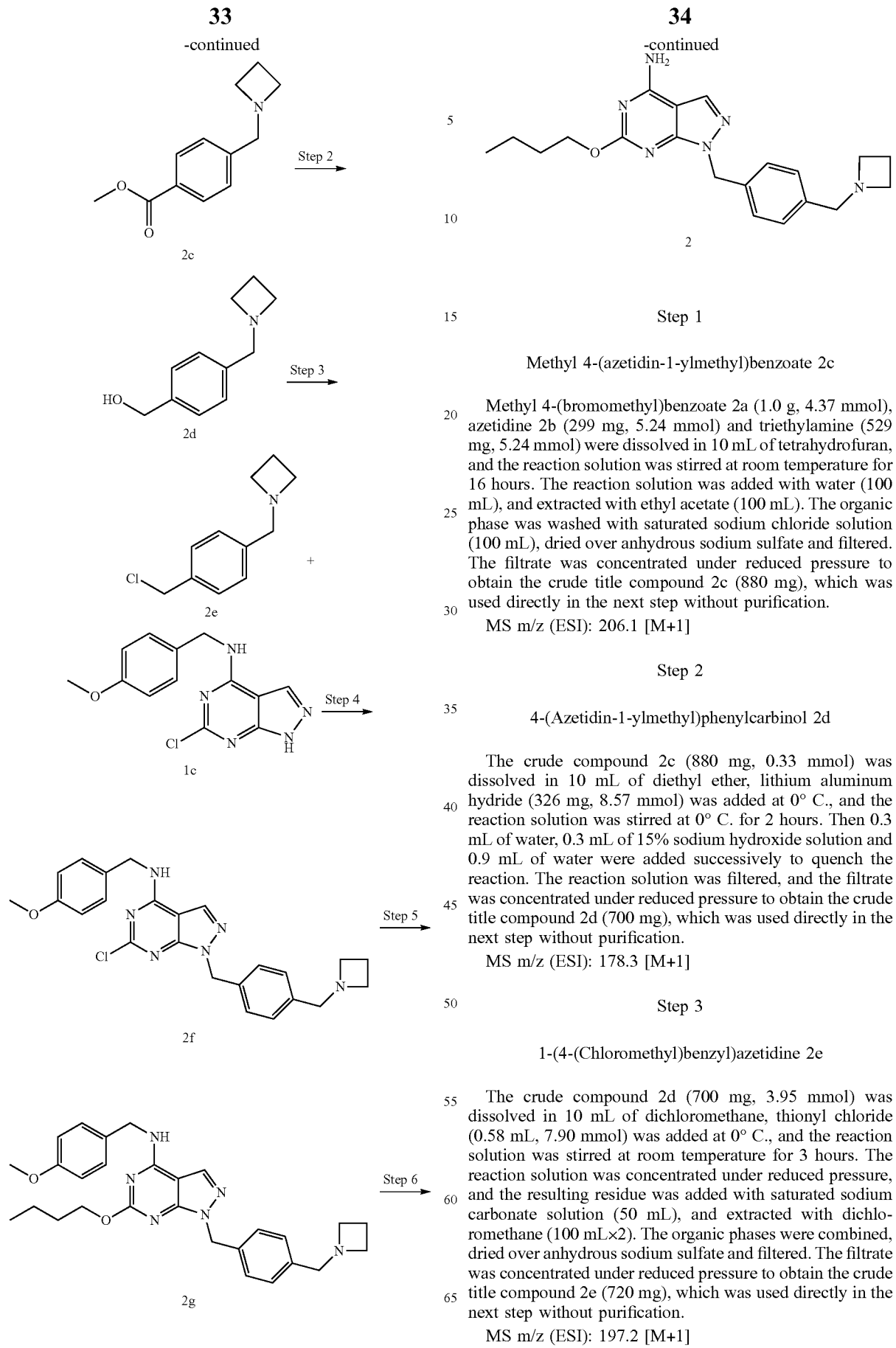

Step 1

Methyl 4-(azetidin-1-ylmethyl)benzoate 2c

Methyl 4-(bromomethyl)benzoate 2a (1.0 g, 4.37 mmol), azetidine 2b (299 mg, 5.24 mmol) and triethylamine (529 mg, 5.24 mmol) were dissolved in 10 mL of tetrahydrofuran, and the reaction solution was stirred at room temperature for 16 hours. The reaction solution was added with water (100 mL), and extracted with ethyl acetate (100 mL). The organic phase was washed with saturated sodium chloride solution (100 mL), dried over anhydrous sodium sulfate and filtered. The filtrate was concentrated under reduced pressure to obtain the crude title compound 2c (880 mg), which was used directly in the next step without purification.

MS m/z (ESI): 206.1 [M+1]

Step 2

4-(Azetidin-1-ylmethyl)phenylcarbinol 2d

The crude compound 2c (880 mg, 0.33 mmol) was dissolved in 10 mL of diethyl ether, lithium aluminum hydride (326 mg, 8.57 mmol) was added at 0° C., and the reaction solution was stirred at 0° C. for 2 hours. Then 0.3 mL of water, 0.3 mL of 15% sodium hydroxide solution and 0.9 mL of water were added successively to quench the reaction. The reaction solution was filtered, and the filtrate was concentrated under reduced pressure to obtain the crude title compound 2d (700 mg), which was used directly in the next step without purification.

MS m/z (ESI): 178.3 [M+1]

Step 3

1-(4-(Chloromethyl)benzyl)azetidine 2e

The crude compound 2d (700 mg, 3.95 mmol) was dissolved in 10 mL of dichloromethane, thionyl chloride (0.58 mL, 7.90 mmol) was added at 0° C., and the reaction solution was stirred at room temperature for 3 hours. The reaction solution was concentrated under reduced pressure, and the resulting residue was added with saturated sodium carbonate solution (50 mL), and extracted with dichloromethane (100 mL×2). The organic phases were combined, dried over anhydrous sodium sulfate and filtered. The filtrate was concentrated under reduced pressure to obtain the crude title compound 2e (720 mg), which was used directly in the next step without purification.

MS m/z (ESI): 197.2 [M+1]

Step 4

1-(4-(Azetidin-1-ylmethyl)benzyl)-6-chloro-N-(4-methoxybenzyl)-1H-pyrazolo[3,4-d]pyrimidin-4-amine 2f Compound 1c (600 mg, 2.07 mmol), the crude compound 2e (405 mg, 2.07 mmol) and potassium carbonate (286 mg, 2.07 mmol) were dissolved in 10 mL of N,N-dimethylformamide, and the reaction solution was stirred at room temperature for 16 hours. The reaction solution was concentrated under reduced pressure, and the resulting residue was purified by silica gel column chromatography with elution system A to obtain the title compound 2f (300 mg, yield: 32.3%).

MS m/z (ESI): 449.2 [M+1]

Step 5

1-(4-(Azetidin-1-ylmethyl)benzyl)-6-butoxy-N-(4-methoxybenzyl)-1H-pyrazolo[3,4-d]pyrimidin-4-amine 2g Compound 2f (150 mg, 0.33 mmol), sodium n-butoxide (0.7 mL, 1.40 mmol) and 2 mL of n-butanol were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 2g (60 mg, yield: 36.9%).

MS m/z (ESI): 487.3 [M+1]

Step 6

1-(4-(Azetidin-1-ylmethyl)benzyl)-6-butoxy-1H-pyrazolo[3,4-d]pyrimidin-4-amine 2

Compound 2g (60 mg, 0.12 mmol) and 2 mL of trifluoroacetic acid were added to a reaction flask, heated to reflux, and stirred for 24 hours. The reaction solution was cooled to room temperature, and concentrated under reduced pressure. The reaction mixture was added with a solution of 7 N ammonia in methanol (1 mL), and concentrated under reduced pressure. The resulting residue was purified by high performance liquid chromatography (Waters-2767, elution system: 10 mmoL/L ammonium bicarbonate, water, acetonitrile) to obtain the title compound 2 (15 mg, yield: 33.2%).

MS m/z (ESI): 367.2 [M+1]

$^1$H NMR (400 MHz, CD$_3$OD) δ 7.97 (s, 1H), 7.34-7.26 (m, 4H), 5.44 (s, 2H), 4.39 (t, 2H), 3.77 (s, 2H), 3.47 (t, 4H), 2.22-2.18 (m, 2H), 1.80-1.76 (m, 2H), 1.55-1.49 (m, 2H), 1.01 (t, 3H).

Example 3

6-Butoxy-1-(4-(piperidin-1-ylmethyl)benzyl)-1H-pyrazolo[3,4-d]pyrimidin-4-amine 3

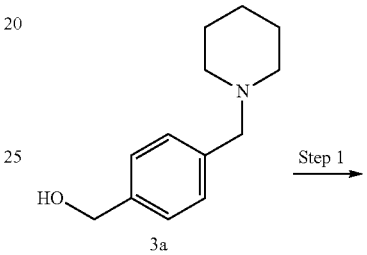

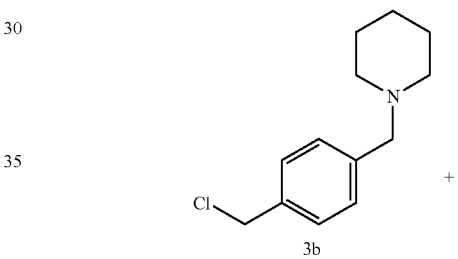
3a

3b

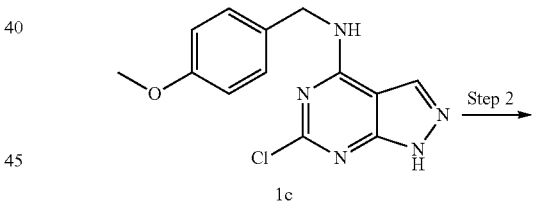
1c

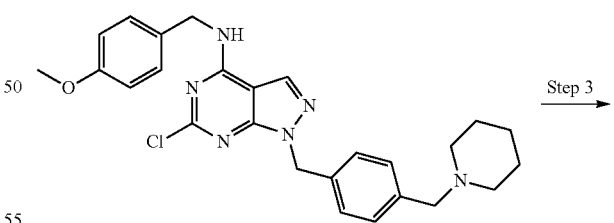
3c

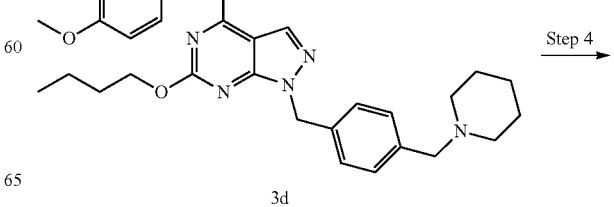
3d

-continued

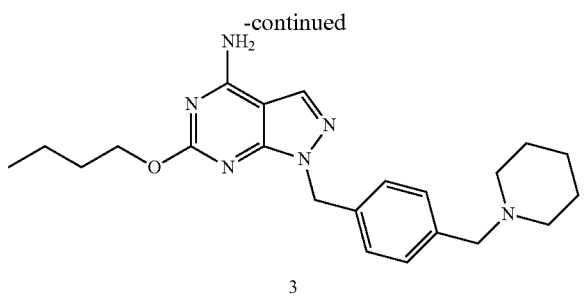

3

Step 1

1-(4-(Chloromethyl)benzyl)piperidine 3b 4-(Piperidin-1-ylmethyl)phenylcarbinol 3a (1.17 g, 5.70 mmol, prepared according to the known method disclosed in "*Journal of Medicinal Chemistry*, 2003, 46(8), 1523-1530") was dissolved in 20 mL of dichloromethane, thionyl chloride (0.83 mL, 11.4 mmol) was added at 0° C., and the reaction solution was stirred at room temperature for 3 hours. The reaction solution was warmed up to room temperature, and concentrated under reduced pressure. The reaction mixture was added with saturated sodium carbonate solution (50 mL), and extracted with dichloromethane (100 mL×2). The organic phases were combined, dried over anhydrous sodium sulfate and filtered. The filtrate was concentrated under reduced pressure to obtain the crude title compound 3b (1.2 g), which was used directly in the next step without purification.

MS m/z (ESI): 224.2 [M+1]

Step 2

6-Chloro-N-(4-methoxybenzyl)-1-(4-(piperidin-1-ylmethyl)benzyl)-1H-pyrazolo[3,4-d]pyrimidin-4-amine 3c Compound 1c (1.5 g, 5.18 mmol), the crude compound 3b (1.16 g, 5.18 mmol) and potassium carbonate (716 mg, 5.18 mmol) were dissolved in 20 mL of N,N-dimethylformamide, and the reaction solution was stirred at room temperature for 16 hours. The reaction solution was concentrated under reduced pressure, and the resulting residue was purified by silica gel column chromatography with elution system A to obtain the title compound 3c (400 mg, yield: 16.2%).

MS m/z (ESI): 477.3 [M+1]

Step 3

6-Butoxy-N-(4-methoxybenzyl)-1-(4-(piperidin-1-ylmethyl)benzyl)-1H-pyrazolo[3,4-d]pyrimidin-4-amine 3d Compound 3c (100 mg, 0.21 mmol), sodium n-butoxide (0.2 mL, 0.80 mmol) and 1 mL of n-butanol were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 3d (50 mg, yield: 46.3%).

MS m/z (ESI): 515.3 [M+1]

Step 4

6-Butoxy-1-(4-(piperidin-1-ylmethyl)benzyl)-1H-pyrazolo[3,4-d]pyrimidin-4-amine 3

Compound 3d (60 mg, 0.12 mmol) and 2 mL of trifluoroacetic acid were added to a reaction flask. The reaction solution was heated to reflux, and stirred for 24 hours. The reaction solution was cooled to room temperature, and concentrated under reduced pressure. The reaction mixture was added with a solution of 7 N ammonia in methanol (1 mL), and concentrated under reduced pressure. The resulting residue was purified by thin layer chromatography with developing system A to obtain the title compound 3 (20 mg, yield: 49.5%).

MS m/z (ESI): 395.3 [M+1]

$^1$H NMR (400 MHz, CD$_3$OD) δ 7.99 (s, 1H), 7.47-7.38 (m, 4H), 5.49 (s, 2H), 4.39 (t, 2H), 4.18 (s, 2H), 3.09-3.00 (m, 4H), 1.81-1.76 (m, 6H), 1.68-1.62 (m, 2H), 1.55-1.49 (m, 2H), 1.00 (t, 3H).

Example 4

6-Butoxy-1-(3-(pyrrolidin-1-ylmethyl)benzyl)-1H-pyrazolo[3,4-d]pyrimidin-4-amine 4

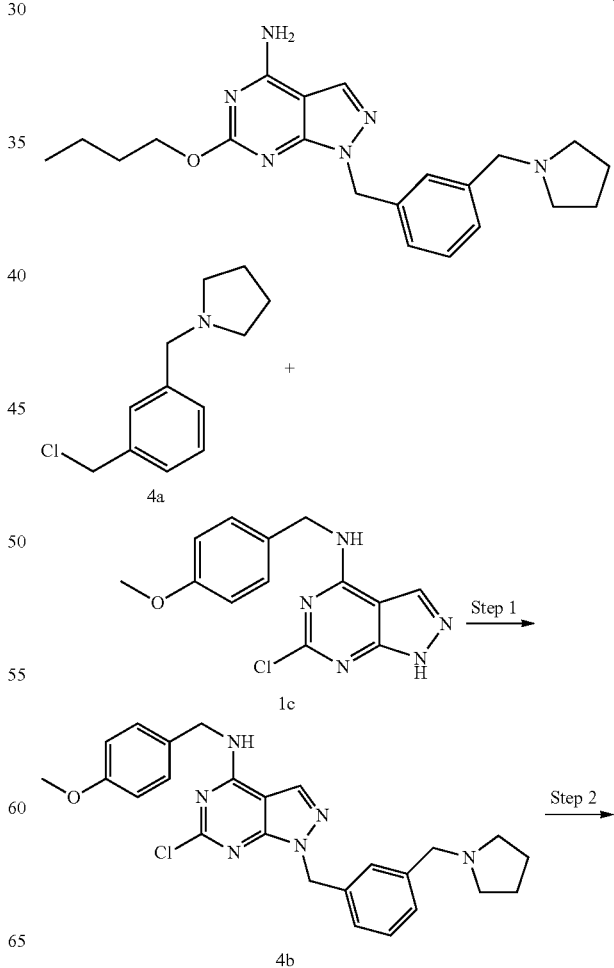

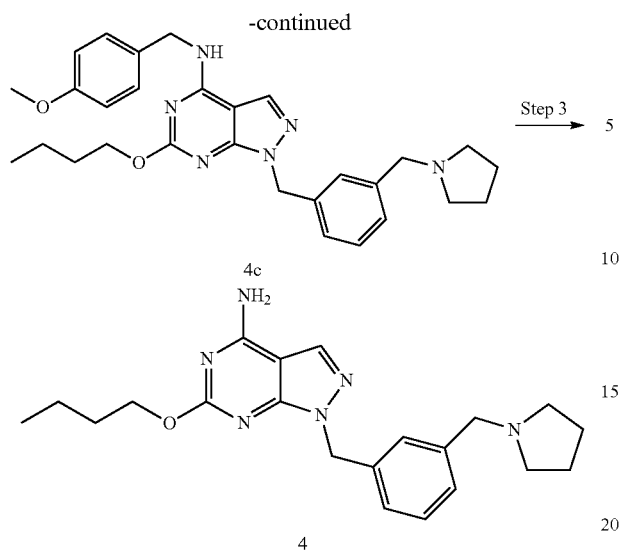

Step 1

6-Chloro-N-(3-methoxybenzyl)-1-(4-(pyrrolidin-1-ylmethyl)benzyl)-1H-pyrazolo[3,4-d]pyrimidin-4-amine 4b Compound 1c (1.0 g, 3.45 mmol), 1-(3-(chloromethyl) benzyl)pyrrolidine 4a (724 mg, 3.45 mmol, prepared according to the method disclosed in the patent application "WO2016040419") and potassium carbonate (377 mg, 3.45 mmol) were dissolved in 10 mL of N,N-dimethylformamide. The reaction was stopped after stirring at room temperature for 16 hours. The reaction solution was concentrated under reduced pressure, and the resulting residue was purified by silica gel column chromatography with elution system A to obtain the title compound 4b (300 mg, yield: 18.7%).

MS m/z (ESI): 463.2 [M+1]

Step 2

6-Butoxy-N-(3-methoxybenzyl)-1-(4-(pyrrolidin-1-ylmethyl)benzyl)-1H-pyrazolo[3,4-d]pyrimidin-4-amine 4c Compound 4b (300 mg, 0.65 mmol), sodium n-butoxide (1.3 mL, 2.60 mmol) and 2 mL of n-butanol were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 4c (140 mg, yield: 43.1%).

MS m/z (ESI): 501.2 [M+1]

Step 3

6-Butoxy-1-(3-(pyrrolidin-1-ylmethyl)benzyl)-1H-pyrazolo[3,4-d]pyrimidin-4-amine 4

Compound 4c (140 mg, 0.08 mmol) and 2 mL of trifluoroacetic acid were added to a reaction flask, heated to reflux, and stirred for 24 hours. The reaction solution was cooled to room temperature, and concentrated under reduced pressure. The reaction mixture was added with a solution of 7 N ammonia in methanol (1 mL), and concentrated under reduced pressure. The resulting residue was purified by high performance liquid chromatography (Waters-2767, elution system: 10 mmoL/L ammonium bicarbonate, water, acetonitrile) to obtain the title compound 4 (60 mg, yield: 56.3%).

MS m/z (ESI): 381.2 [M+1]

$^1$H NMR (400 MHz, CD$_3$OD) δ 7.98 (s, 1H), 7.35-725 (m, 4H), 5.47 (s, 2H), 4.39 (t, 2H), 3.81 (s, 2H), 2.76-2.70 (m, 4H), 1.98-1.93 (m, 4H), 1.79-1.76 (m, 2H), 1.55-1.50 (m, 2H), 1.01 (t, 3H).

Example 5

1-(3-(Azetidin-1-ylmethyl)benzyl)-6-butoxy-1H-pyrazolo[3,4-d]pyrimidin-4-amine 5

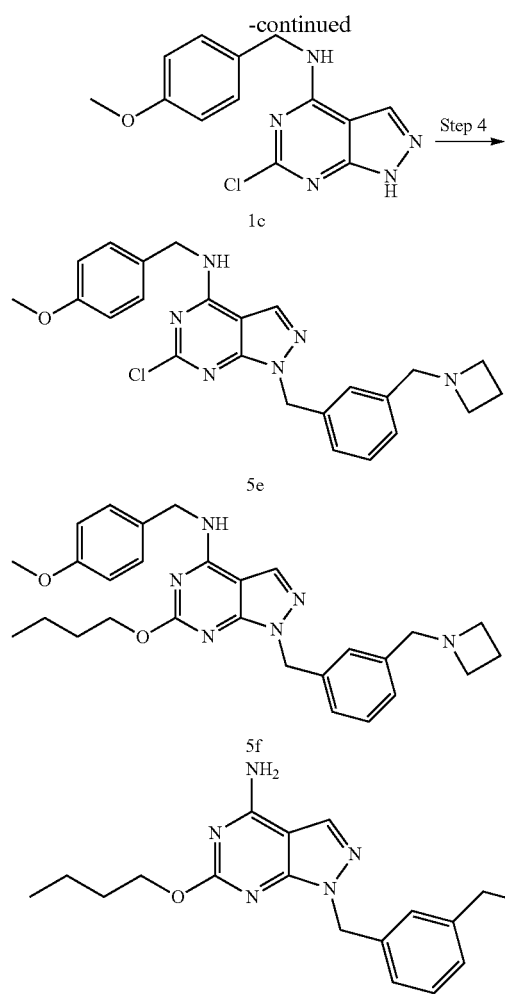

0.9 mL of water were added successively to quench the reaction. The reaction solution was filtered, and the filtrate was concentrated under reduced pressure to obtain the crude title compound 5c (700 mg), which was used directly in the next step without purification.

MS m/z (ESI): 178.3 [M+1]

Step 3

1-(3-(Chloromethyl)benzyl)azetidine 5d

The crude compound 5c (700 mg, 3.95 mmol) was dissolved in 10 mL of dichloromethane, thionyl chloride (0.58 mL, 7.90 mmol) was added at 0° C., and the reaction solution was stirred at room temperature for 3 hours. The reaction solution was concentrated under reduced pressure, added with saturated sodium carbonate solution (50 mL), and extracted with dichloromethane (100 mL×2). The organic phases were combined, dried over anhydrous sodium sulfate and filtered. The filtrate was concentrated under reduced pressure to obtain the crude title compound 5d (700 mg), which was used directly in the next step without purification.

MS m/z (ESI): 197.2 [M+1]

Step 4

1-(3-(Azetidin-1-ylmethyl)benzyl)-6-chloro-N-(4-methoxybenzyl)-1H-pyrazolo[3,4-d]pyrimidin-4-amine 5e Compound 1c (300 mg, 1.04 mmol), the crude compound 5d (203 mg, 1.04 mmol) and potassium carbonate (144 mg, 1.04 mmol) were dissolved in 5 mL of N,N-dimethylformamide, and the reaction solution was stirred at room temperature for 16 hours. The reaction solution was concentrated under reduced pressure, and the resulting residue was purified by silica gel column chromatography with elution system A to obtain the title compound 5e (30 mg, yield: 6.5%).

MS m/z (ESI): 449.2 [M+1]

Step 5

1-(3-(Azetidin-1-ylmethyl)benzyl)-6-butoxy-N-(4-methoxybenzyl)-1H-pyrazolo[3,4-d]pyrimidin-4-amine 5f Compound 5e (50 mg, 0.11 mmol), sodium n-butoxide (0.2 mL, 0.40 mmol) and 1 mL of n-butanol were added to a microwave tube successively, heated to 160° C. and stirred for 1.5 hours. The reaction solution was cooled to room temperature, and concentrated under reduced pressure. The resulting residue was purified by thin layer chromatography with developing system A to obtain the title compound 5f (35 mg, yield: 64.8%).

MS m/z (ESI): 487.3 [M+1]

Step 1

Methyl 3-(azetidin-1-ylmethyl)benzoate 5b

Methyl 3-(bromomethyl)benzoate 5a (1.0 g, 4.37 mmol), azetidine 2b (299 mg, 5.24 mmol) and triethylamine (529 mg, 5.24 mmol) were dissolved in 10 mL of tetrahydrofuran, and the reaction solution was stirred at room temperature for 16 hours. The reaction solution was added with water (100 mL), and extracted with ethyl acetate (100 mL). The organic phase was washed with saturated sodium chloride solution (100 mL), dried over anhydrous sodium sulfate and filtered. The filtrate was concentrated under reduced pressure to obtain the crude title compound 5b (840 mg), which was used directly in the next step without purification.

MS m/z (ESI): 206.1 [M+1]

Step 2

3-(Azetidin-1-ylmethyl)phenylcarbinol 5c

The crude compound 5b (840 mg, 4.09 mmol) was dissolved in 10 mL of diethyl ether, lithium aluminum hydride (310 mg, 8.19 mmol) was added at 0° C., and the reaction solution was stirred at 0° C. for 2 hours. Then 0.3 mL of water, 0.3 mL of 15% sodium hydroxide solution and Step 6

1-(3-(Azetidin-1-ylmethyl)benzyl)-6-butoxy-1H-pyrazolo[3,4-d]pyrimidin-4-amine 5

Compound 5f (35 mg, 0.07 mmol) and 1 mL of trifluoroacetic acid were added to a reaction flask. The reaction solution was heated to reflux, and stirred for 24 hours. The reaction solution was cooled to room temperature, and concentrated under reduced pressure. The reaction mixture was added with a solution of 7 N ammonia in methanol (1 mL), and concentrated under reduced pressure. The resulting residue was purified by high performance liquid chromatography (Waters-2767, elution system: 10 mmoL/L ammonium bicarbonate, water, acetonitrile) to obtain the title compound 5 (2.0 mg, yield: 7.9%).

MS m/z (ESI): 367.2 [M+1]

$^{1}$H NMR (400 MHz, CD$_{3}$OD) δ 7.98 (s, 1H), 7.30-7.28 (m, 1H), 7.22-7.19 (m, 3H), 5.45 (s, 2H), 4.39 (t, 2H), 3.60 (s, 2H), 3.28 (t, 4H), 2.12-2.09 (m, 2H), 1.80-1.76 (m, 2H), 1.55-1.49 (m, 2H), 1.00 (t, 3H).

Example 6

6-Butoxy-1-(3-(piperidin-1-ylmethyl)benzyl)-1H-pyrazolo[3,4-d]pyrimidin-4-amine 6

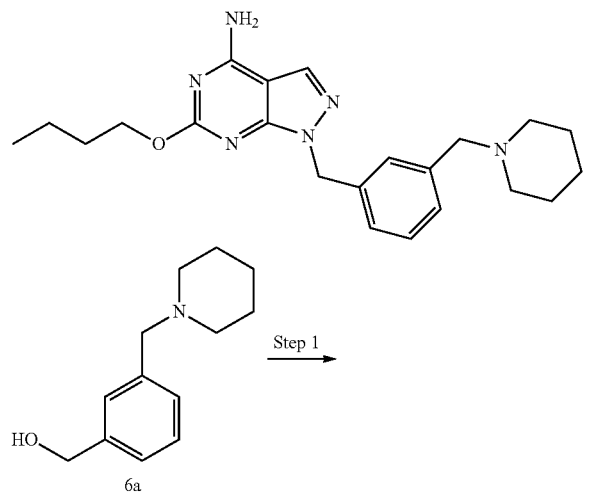

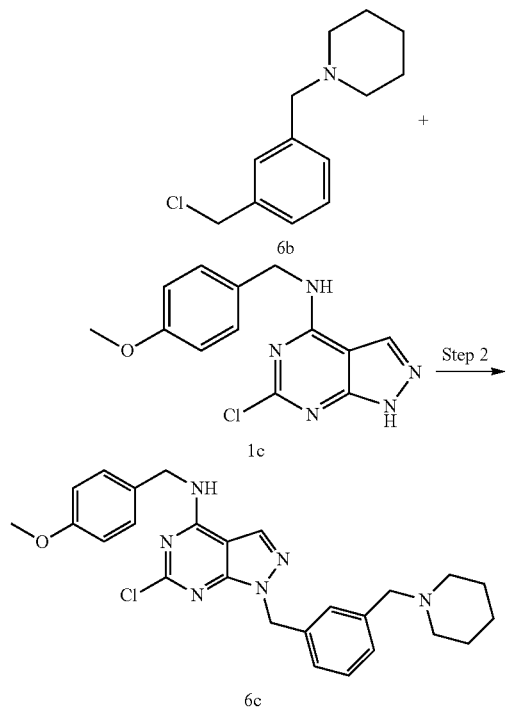

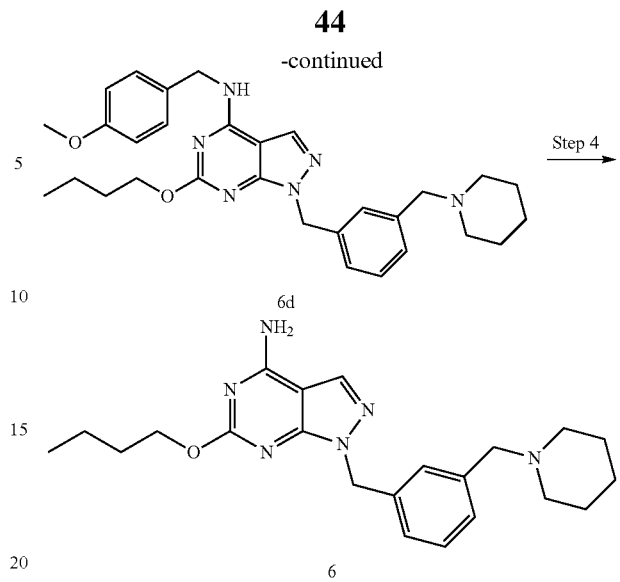

Step 1

1-(3-(Chloromethyl)benzyl)piperidine 6b 3-(Piperidin-1-ylmethyl)phenylcarbinol 6a (1.7 g, 8.28 mmol, prepared according to the known method disclosed in "Bioorganic & Medicinal Chemistry, 2004, 12(10), 2727-2736") was dissolved in 20 mL of dichloromethane, thionyl chloride (1.2 mL, 16.56 mmol) was added at 0° C., and the reaction solution was stirred at room temperature for 3 hours. The reaction solution was concentrated under reduced pressure, added with saturated sodium carbonate solution (50 mL), and extracted with dichloromethane (100 mL×2). The organic phases were combined, dried over anhydrous sodium sulfate and filtered. The filtrate was concentrated under reduced pressure to obtain the crude title compound 6b (1.7 g), which was used directly in the next step without purification.

MS m/z (ESI): 224.2 [M+1]

Step 2

6-Chloro-N-(3-methoxybenzyl)-1-(4-(piperidin-1-ylmethyl)benzyl)-1H-pyrazolo[3,4-d]pyrimidin-4-amine 6c Compound 1c (300 mg, 1.04 mmol), the crude compound 6b (232 mg, 1.04 mmol) and potassium carbonate (144 mg, 1.04 mmol) were dissolved in 5 mL of N,N-dimethylformamide. The reaction was stopped after stirring at room temperature for 16 hours. The reaction solution was concentrated under reduced pressure, and the resulting residue was purified by silica gel column chromatography with elution system A to obtain the title compound 6c (50 mg, yield: 10.1%).

MS m/z (ESI): 477.3 [M+1]

Step 3

6-Butoxy-N-(3-methoxybenzyl)-1-(4-(piperidin-1-ylmethyl)benzyl)-1H-pyrazolo[3,4-d]pyrimidin-4-amine 6d Compound 6c (50 mg, 0.10 mmol), sodium n-butoxide (0.2 mL, 0.40 mmol) and 1 mL of n-butanol were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 6d (30 mg, yield: 55.5%).

MS m/z (ESI): 515.3 [M+1]

Step 4

6-Butoxy-1-(3-(piperidin-1-ylmethyl)benzyl)-1H-pyrazolo[3,4-d]pyrimidin-4-amine 6

Compound 6d (30 mg, 0.06 mmol) and 2 mL of trifluoroacetic acid were added to a reaction flask, heated to reflux, and stirred for 24 hours. The reaction was stopped, and the reaction solution was concentrated under reduced pressure and added with a solution of 7 N ammonia in methanol (1 mL). The reaction solution was concentrated under reduced pressure, and the residue was purified by thin layer chromatography with developing system A to obtain the title compound 6 (7.0 mg, yield: 29.2%).

MS m/z (ESI): 395.3 [M+1]
$^1$H NMR (400 MHz, CD$_3$OD) δ 7.99 (s, 1H), 738-7.31 (m, 4H), 5.48 (s, 2H), 4.38 (t, 2H), 3.86 (s, 2H), 2.87-2.80 (m, 4H), 1.79-1.75 (m, 2H), 1.71-1.68 (m, 4H), 1.54-1.40 (m, 4H), 1.00 (t, 3H).

Example 7

6-(2-Methoxyethoxy)-1-(4-(pyrrolidin-1-ylmethyl)benzyl)-1H-pyrazolo[3,4-d]pyrimidin-4-amine 7

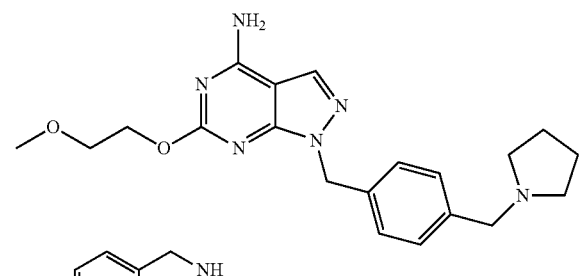

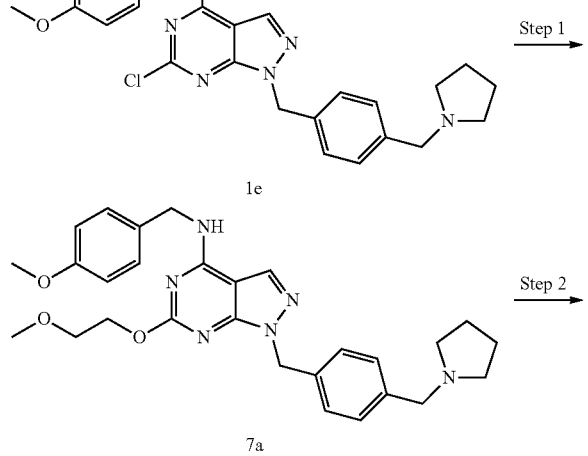

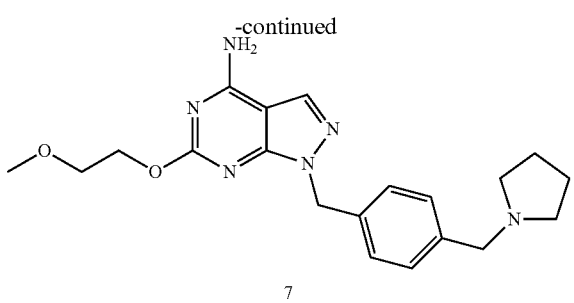

Step 1

N-(4-Methoxybenzyl)-6-(2-methoxyethoxy)-1-(4-(pyrrolidin-1-ylmethyl)benzyl)-1H-pyrazolo[3,4-d]pyrimidin-4-amine 7a Compound 1e (90 mg, 0.19 mmol), sodium 2-methoxyethanol (0.3 mL, 0.60 mmol) and 1 mL of 2-methoxyethanol were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 7a (30 mg, yield: 30.7%).

MS m/z (ESI): 503.3 [M+1]

Step 2

6-(2-Methoxyethoxy)-1-(4-(pyrrolidin-1-ylmethyl)benzyl)-1H-pyrazolo[3,4-d]pyrimidin-4-amine 7

Compound 7a (30 mg, 0.06 mmol) and 5 mL of trifluoroacetic acid were added to a reaction flask, heated to 100° C., and stirred for 2 hours. The reaction solution was cooled to room temperature, and concentrated under reduced pressure. The resulting residue was purified by high performance liquid chromatography (Waters-2767, elution system: 10 mmoL/L ammonium bicarbonate, water, acetonitrile) to obtain the title compound 7 (5 mg, yield: 19.7%).

MS m/z (ESI): 383.2 [M+1]
$^1$H NMR (400 MHz, CD$_3$OD) δ 7.96 (s, 1H), 7.30-7.28 (d, 2H), 7.25-7.23 (d, 2H), 5.42 (s, 2H), 4.51-4.48 (t, 2H), 3.74-3.72 (t, 2H), 3.65 (s, 2H), 3.39 (s, 3H), 2.57 (s, 4H), 1.81-1.78 (m, 4H).

Example 8

6-((1-Methoxypropan-2-yl)oxy)-1-(4-(pyrrolidin-1-ylmethyl)benzyl)-1H-pyrazolo[3,4-d]pyrimidin-4-amine 8

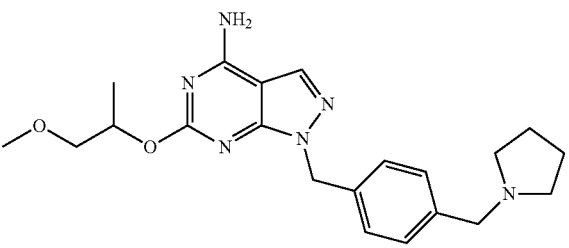

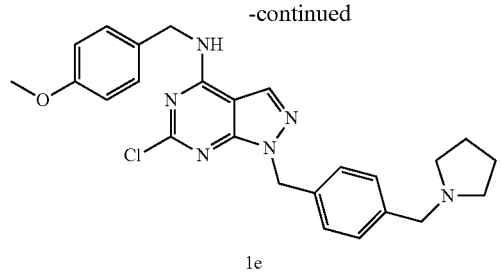

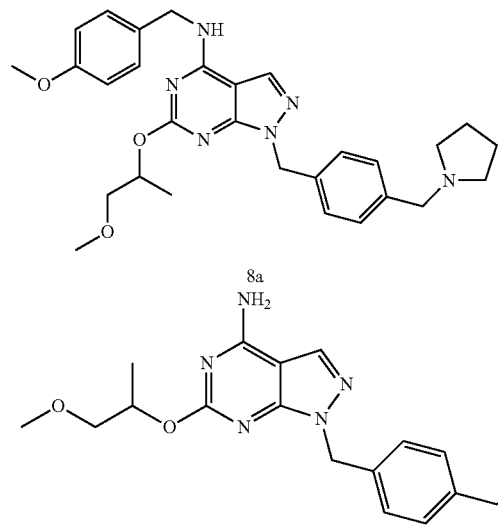

Step 1

N-(4-Methoxybenzyl)-6-((1-methoxypropan-2-yl)oxy)-1-(4-(pyrrolidin-1-ylmethyl)benzyl)-1H-pyrazolo[3,4-d]pyrimidin-4-amine 8a Compound 1e (200 mg, 0.43 mmol), 2-methoxy-1-methyl-ethoxy sodium (96.9 mg, 0.86 mmol) and 5 mL of propylene glycol methyl ether were added to a microwave tube successively, heated to 160° C. and stirred for 1.5 hours. The reaction solution was cooled to room temperature, and concentrated under reduced pressure. The resulting residue was purified by silica gel column chromatography with elution system A to obtain the title compound 8a (150 mg, yield: 67.2%).

MS m/z (ESI): 517.3 [M+1]

Step 2

6-((1-Methoxypropan-2-yl)oxy)-1-(4-(pyrrolidin-1-ylmethyl)benzyl)-1H-pyrazolo[3,4-d]pyrimidin-4-amine 8

Compound 8a (80 mg, 0.15 mmol) and 5 mL of trifluoroacetic acid were added to a reaction flask, heated to 80° C., and stirred for 1 hour. The reaction solution was cooled to room temperature, and concentrated under reduced pressure. The resulting residue was purified by high performance liquid chromatography (Waters-2767, elution system: 10 mmoL/L ammonium bicarbonate, water, acetonitrile) to obtain the title compound 8 (20 mg, yield: 32.6%).

MS m/z (ESI): 397.2 [M+1]

$^1$H NMR (400 MHz, CD$_3$OD) δ 7.95 (s, 1H), 7.35-7.33 (d, 2H), 7.29-7.27 (d, 2H), 5.43 (m, 3H), 3.83 (s, 2H), 3.60-3.52 (m, 2H), 3.37 (s, 3H), 2.76 (s, 4H), 1.87 (s, 4H), 1.34-1.32 (t, 3H).

Example 9

6-Butoxy-1-(3-fluoro-4-(pyrrolidin-1-ylmethyl)benzyl)-1H-pyrazolo[3,4-d]pyrimidin-4-amine 9

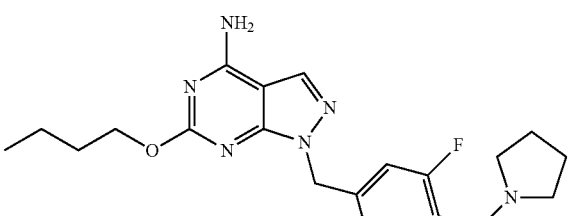

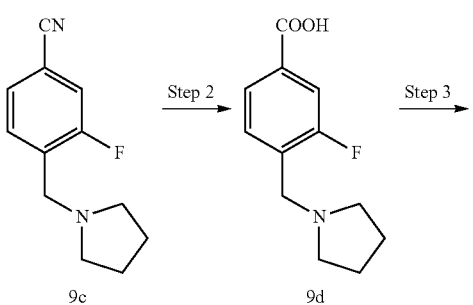

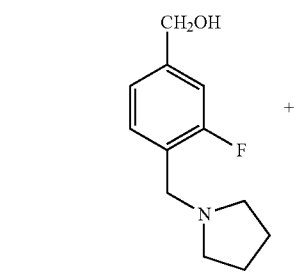

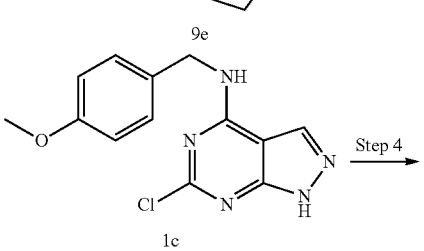

49

-continued

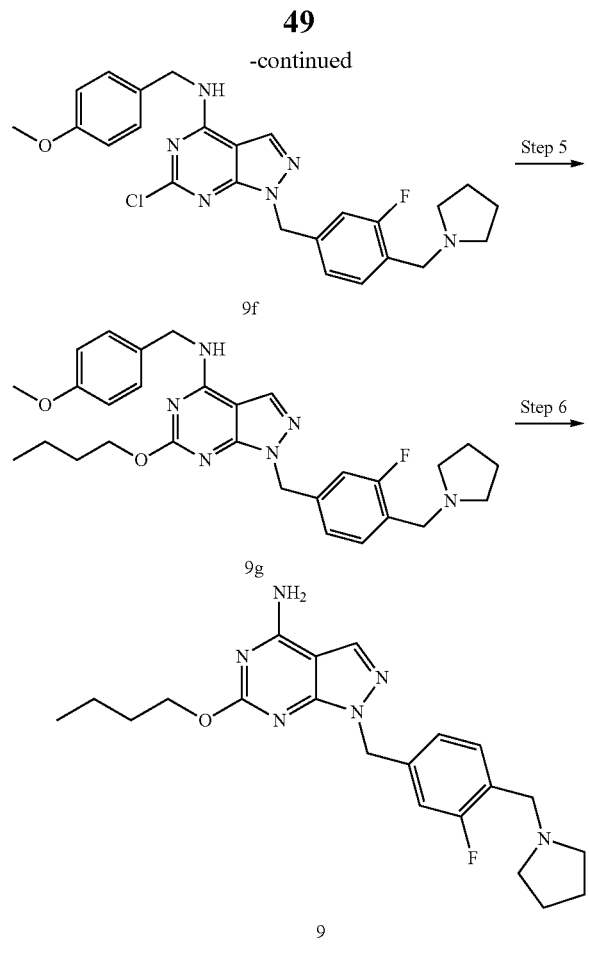

Step 1

3-Fluoro-4-(pyrrolidin-1-ylmethyl)benzonitrile 9c 4-(Bromomethyl)-3-fluorobenzonitrile 9a (1 g, 4.67 mmol), pyrrolidine 9b (332 mg, 4.67 mmol) and N,N-diisopropylethylamine (1.21 g, 9.34 mmol) were dissolved in 10 mL of acetonitrile. After stirring for 2 hours, the reaction solution was concentrated under reduced pressure to obtain the crude title compound 9c (1 g), which was used directly in the next step without purification.

MS m/z (ESI): 205.4 [M+1]

Step 2

3-Fluoro-4-(pyrrolidin-1-ylmethyl)benzoic acid 9d

The crude compound 9c (1 g, 4.9 mmol) was dissolved in a mixed solvent of 5 mL of sulfuric acid, 5 mL of water and 10 mL of acetic acid. The reaction was stopped after stirring at 90° C. for 16 hours. The reaction solution was cooled to room temperature, and concentrated under reduced pressure. The residue was added with methanol, and filtered to remove insoluble matters. The filtrate was concentrated under reduced pressure to obtain the crude title compound 9d (1 g), which was used directly in the next step without purification.

MS m/z (ESI): 224.4 [M+1]

50

Step 3

(3-Fluoro-4-(pyrrolidin-1-ylmethyl)phenyl)methanol 9e

The crude compound 9d (1 g, 4.48 mmol) was dissolved in 20 mL of tetrahydrofuran. The reaction solution was cooled to 0° C., added with lithium aluminum hydride (607 mg, 17.9 mmol) and stirred for 3 hours. Then 1 mL of water, 1 mL of 2N sodium hydroxide solution and 3 mL of water were added successively to quench the reaction. The reaction solution was filtered, and the filtrate was collected and concentrated under reduced pressure to obtain the crude title compound 9e (820 mg), which was used directly in the next step without purification.

MS m/z (ESI): 210.4 [M+1]

Step 4

6-Chloro-1-(3-fluoro-4-(pyrrolidin-1-ylmethyl)benzyl)-N-(4-methoxybenzyl)-1H-pyrazolo[3,4-d]pyrimidin-4-amine 9f The crude compound 9e (100 mg, 0.48 mmol), compound 1c (141.34 mg, 0.48 mmol) and triphenylphosphine (192 mg, 0.73 mmol) were dissolved in 10 mL of 1,4-dioxane, and diisopropyl azodicarboxylate (148 mg, 0.73 mmol) was then added dropwise. The reaction solution was warmed up to 85° C., and stirred for 4 hours. The reaction solution was cooled to room temperature, and concentrated under reduced pressure. The resulting residue was purified by silica gel column chromatography with elution system A to obtain the title compound 9f (90 mg, yield: 38.3%).

MS m/z (ESI): 481.4 [M+1]

Step 5

6-Butoxy-1-(3-fluoro-4-(pyrrolidin-1-ylmethyl)benzyl)-N-(4-methoxybenzyl)-1H-pyrazolo[3,4-d]pyrimidin-4-amine 9g Compound 9f (90 mg, 0.19 mmol), sodium n-butoxide (18 mg, 0.18 mmol) and 5 mL of n-butanol were added to a microwave tube successively, heated to 160° C. and stirred for 1.5 hours. The reaction was stopped, and the reaction solution was cooled to room temperature and concentrated under reduced pressure. The resulting residue was purified by silica gel column chromatography with elution system A to obtain the title compound 9g (35 mg, yield: 36.1%).

MS m/z (ESI): 519.5 [M+1]

Step 6

6-Butoxy-1-(3-fluoro-4-(pyrrolidin-1-ylmethyl)benzyl)-1H-pyrazolo[3,4-d]pyrimidin-4-amine 9

Compound 9g (35 mg, 0.07 mmol) and 10 mL of trifluoroacetic acid were added to a sealed tube, heated to 100° C., and stirred for 1 hour. The reaction was stopped, and the reaction solution was cooled to room temperature and concentrated under reduced pressure. The resulting residue was purified by high performance liquid chromatography (Waters-2767, elution system: 10 mmoL/L ammonium bicarbonate, water, acetonitrile) to obtain the title compound 9 (20 mg, yield: 74.3%).

MS m/z (ESI): 399.5 [M+1]

¹H NMR (400 MHz, CD₃OD) δ 7.97 (s, 1H), 7.37-7.33 (m, 1H), 7.07-6.99 (m, 2H), 5.42 (s, 2H), 4.38-4.35 (t, 2H), 3.68 (s, 2H), 2.56 (s, 4H), 1.79-1.73 (m, 6H), 1.52-1.46 (m, 2H), 0.99-0.96 (t, 3H).

Example 10

N⁶-Butyl-1-(4-(pyrrolidin-1-ylmethyl)benzyl)-1H-pyrazolo[3,4-d]pyrimidine-4,6-diamine 10

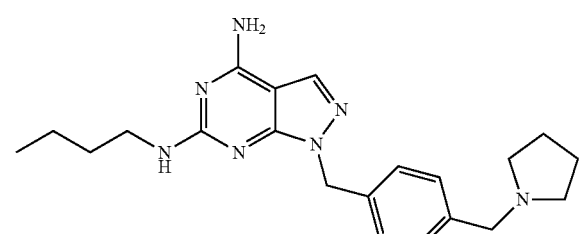

1e

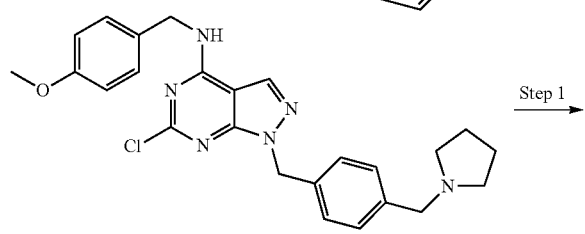

Step 1

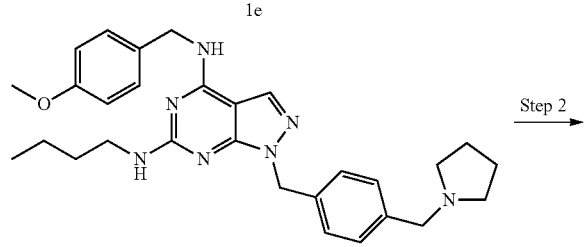

10a

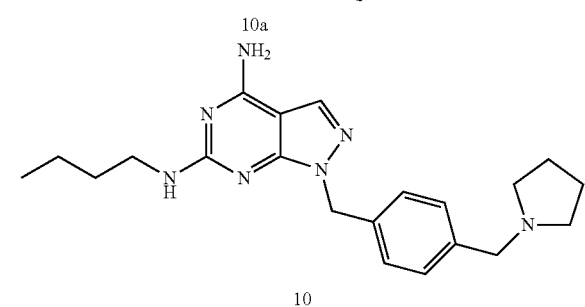

10

Step 1

N⁶-Butyl-N⁴-(4-methoxybenzyl)-1-(4-(pyrrolidin-1-ylmethyl)benzyl)-1H-pyrazolo[3,4-d]pyrimidine-4,6-diamine 10a Compound 1e (50 mg, 0.11 mmol), n-butylamine (23.7 mg, 0.32 mmol) and N,N-diisopropylethylamine (41.9 mg, 0.32 mmol) were added to 5 mL of n-butanol successively. The reaction solution was warmed up to 120° C. and stirred under microwave for 1 hour. The reaction solution was cooled to room temperature, and concentrated under reduced pressure to obtain the crude title compound 10a (20 mg), which was used directly in the next step without purification.

Step 2

N⁶-Butyl-1-(4-(pyrrolidin-1-ylmethyl)benzyl)-1H-pyrazolo[3,4-d]pyrimidine-4,6-diamine 10

The crude compound 10a (20 mg, 0.04 mmol) and 5 mL of trifluoroacetic acid were added to a reaction flask, heated to 100° C., and stirred overnight. The reaction was stopped, and the reaction solution was cooled to room temperature and concentrated under reduced pressure. The resulting residue was purified by high performance liquid chromatography (Waters-2767, elution system: 10 mmoL/L ammonium bicarbonate, water, acetonitrile) to obtain the title compound 10 (15.2 mg, a yellow solid, yield: 62.5%).

MS m/z (ESI): 380.3 [M+1]

¹H NMR (400 MHz, CD₃OD) δ 8.04 (s, 1H), 7.49-7.47 (d, 2H), 7.42-7.40 (d, 2H), 5.44 (s, 2H), 4.34 (s, 2H), 3.49-3.45 (m, 4H), 3.15 (s, 2H), 2.13 (s, 2H), 1.93 (s, 2H), 1.65-1.60 (m, 2H), 1.45-1.39 (m, 2H), 0.98-0.94 (t, 3H).

Example 11

4-Amino-N-propyl-1-(4-(pyrrolidin-1-ylmethyl)benzyl)-1H-pyrazolo[3,4-d]pyrimidine-6-carboxamide 11

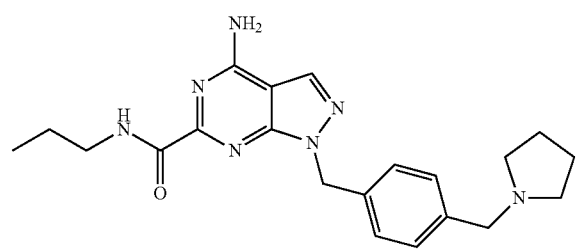

11

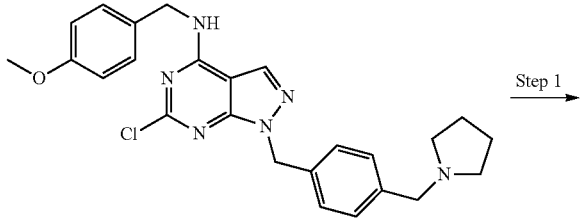

1e

Step 1

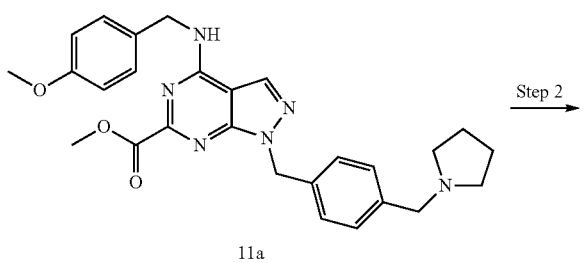

11a

Step 2

-continued

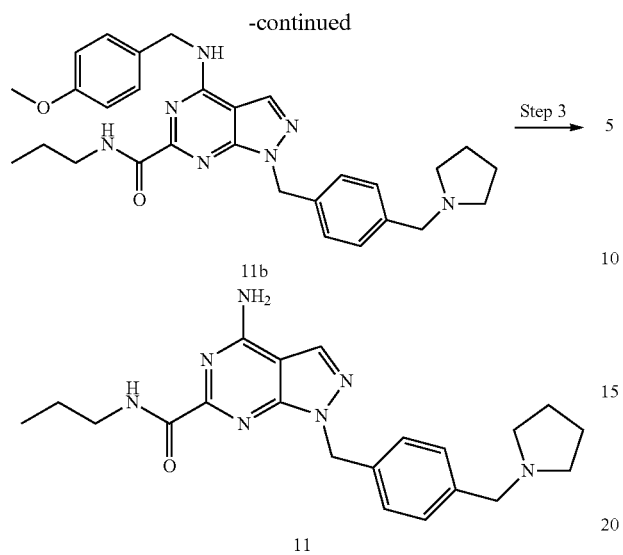

11b

11

Step 1

Methyl 4-((4-methoxybenzyl)amino)-1-(4-(pyrrolidin-1-ylmethyl)benzyl)-1H-pyrazolo[3,4-d]pyrimidine-6-carboxylate 11a Compound 1e (200 mg, 0.43 mmol), palladium acetate (2.9 mg, 0.013 mmol), 4,5-bisdiphenylphosphino-9,9-dimethyloxanthene (15 mg, 0.026 mmol) and triethylamine (44 mg, 0.4 mmol) were dissolved in 3 mL of n-butanol and 3 mL of N,N-dimethylformamide. The reaction system was purged with carbon monoxide three times. The reaction solution was warmed up to 70° C., and stirred for 16 hours. The reaction solution was cooled to room temperature, and concentrated under reduced pressure. The resulting residue was purified by silica gel column chromatography with elution system A to obtain the title compound 11a (150 mg, yield: 71.4%).

MS m/z (ESI): 487.5 [M+1]

Step 2

4-((4-Methoxybenzyl)amino)-N-propyl-1-(4-(pyrrolidin-1-ylmethyl)benzyl)-1H-pyrazolo[3,4-d]pyrimidine-6-carboxamide 11b Compound 11a (50 mg, 0.1 mmol) and n-propylamine (12 mg, 0.2 mmol) were dissolved in 5 mL of ethanol successively. The reaction solution was added to a sealed tube, warmed up to 60° C., and stirred for 16 hours. The reaction was stopped, and the reaction solution was cooled to room temperature and concentrated under reduced pressure to obtain the crude title compound 11b (20 mg), which was used directly in the next step without purification.

Step 3

4-Amino-N-propyl-1-(4-(pyrrolidin-1-ylmethyl)benzyl)-1H-pyrazolo[3,4-d]pyrimidine-6-carboxamide 11

The crude compound 11b (20 mg, 0.04 mmol) and 5 mL of trifluoroacetic acid were added to a reaction flask, heated to 100° C., and stirred for 12 hours. The reaction solution was cooled to room temperature, and concentrated under reduced pressure. The resulting residue was purified by high performance liquid chromatography (Waters-2767, elution system: 10 mmoL/L ammonium bicarbonate, water, acetonitrile) to obtain the title compound 11 (10 mg, yield: 60.3%).

MS m/z (ESI): 394.5 [M+1]

$^1$H NMR (400 MHz, CD$_3$OD) δ 8.12 (s, 1H), 7.28 (m, 4H), 5.64 (s, 2H), 3.62 (s, 2H), 3.41-3.37 (t, 2H), 2.55-2.52 (m, 4H), 1.80-1.77 (m, 4H), 1.70-1.64 (m, 2H), 0.98-1.02 (t, 3H).

Example 12

1-(4-Amino-1-(4-pyrrolidin-1-ylmethyl)benzyl)-1H-pyrazolo[3,4-d]pyrimidin-6-yl)pentan-1-one 12

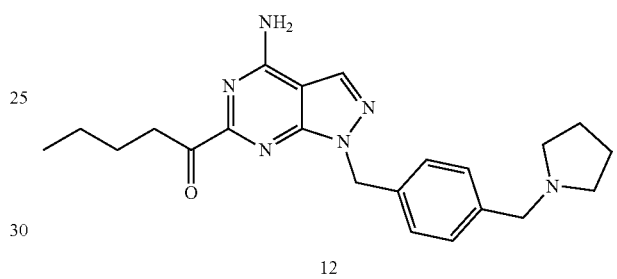

12

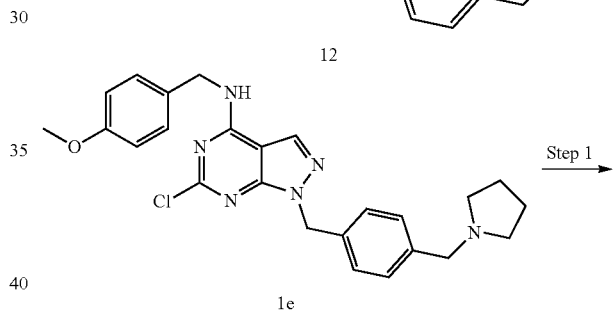

1e

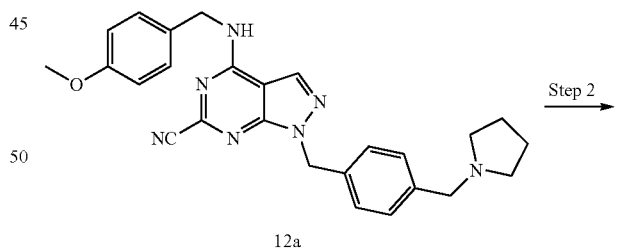

12a

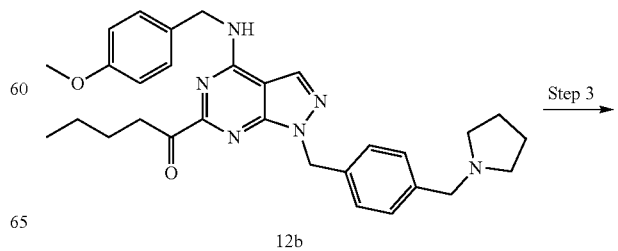

12b

-continued

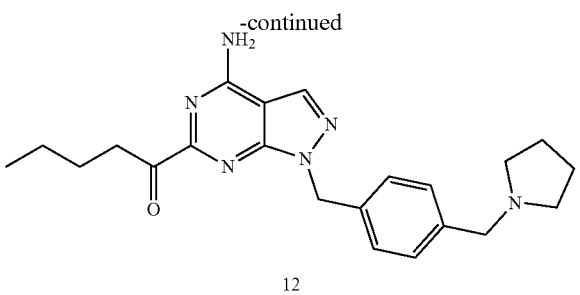

12

Step 1

4-((4-Methoxybenzyl)amino)-1-(4-(pyrrolidin-1-ylmethyl)benzyl)-1H-pyrazolo[3,4-d]pyrimidine-6-carbonitrile 12a Compound 1e (260 mg, 0.56 mmol), tris(dibenzylideneacetone)dipalladium (52 mg, 0.056 mmol), 1,1′-bis(diphenylphosphino)ferrocene (31 mg, 0.056 mmol), zinc cyanide (99 mg, 0.84 mmol) and zinc powder (37 mg, 0.56 mmol) were suspended in 5 mL of N,N-dimethylacetamide. The reaction solution was warmed up to 140° C., and stirred for 16 hours under an argon atmosphere. The reaction solution was cooled to room temperature, and concentrated under reduced pressure. The resulting residue was purified by thin layer chromatography with developing system A to obtain the title compound 12a (160 mg, yield: 63%).

MS m/z (ESI): 454.5 [M+1]

Step 2

1-(4-((4-Methoxybenzyl)amino)-1-(4-(pyrrolidin-1-ylmethyl)benzyl)-1H-pyrazolo[3,4-d]pyrimidin-6-yl)pentan-1-one 12b Compound 12a (160 mg, 0.35 mmol) was dissolved in 5 mL of tetrahydrofuran, and a solution of 2 M n-butylmagnesium chloride in tetrahydrofuran (0.9 mL, 1.77 mmol) was then added at 0° C. The reaction solution was warmed up to 60° C., and stirred for 2 hours under an argon atmosphere. The reaction solution was cooled to room temperature, added with an aqueous solution of ammonium chloride, and extracted with ethyl acetate. The organic phases were combined and concentrated under reduced pressure. The resulting residue was purified by thin layer chromatography with developing system A to obtain the title compound 12b (150 mg, yield: 83%).

MS m/z (ESI): 513.6 [M+1]

Step 3

1-(4-Amino-1-(4-pyrrolidin-1-ylmethyl)benzyl)-1H-pyrazolo[3,4-d]pyrimidin-6-yl)pentan-1-one 12

Compound 12b (150 mg, 0.29 mmol) was dissolved in 10 mL of trifluoroacetic acid. The reaction solution was added to a sealed tube, heated to 110° C., and stirred for 16 hours. The reaction solution was cooled to room temperature, and concentrated under reduced pressure. The resulting residue was purified by high performance liquid chromatography (Waters-2767, elution system: 10 mmoL/L ammonium bicarbonate, water, acetonitrile) to obtain the title compound 12 (19 mg, yield: 17%).

MS m/z (ESI): 393.5 [M+1]
$^1$H NMR (400 MHz, CDCl$_3$): δ 8.01 (s, 1H), 7.35-7.29 (q, 4H), 5.62 (s, 2H), 3.62 (s, 2H), 3.26 (t, 2H), 2.53 (s, 4H), 1.78 (s, 4H), 1.76-1.70 (m, 2H), 1.48-1.42 (m, 2H), 0.98 (t, 3H).

TEST EXAMPLES

Biological Assay

Test Example 1. Determination of Agonistic Activity of the Compounds of the Present Invention on Human TLR7

The activation effect of the compounds of the present invention on the hTLR7 protein expressed by the HEK-Blue™ hTLR7 stably transfected cells was determined by the following experimental method:

I. Experimental Materials and Instruments
1. DMEM (Gibco, 10564-029),
2. Fetal bovine serum (GIBCO, 10099),
3. Penicillin-streptomycin (Gibco, 15140-122),
4. Trypan blue solution (Sigma, T8154-100ML),
5. Flexstation 3 multi-function microplate reader (Molecular Devices),
6. HEK-Blue™ HTLR7 cell line (InvivoGen, hkb-hTLR7),
7. HEK-Blue detection reagent (InvivoGen, hb-det3).

II. Experimental Procedures

A bag of HEK-Blue detection dry powder was dissolved in 50 ml of water free of endotoxin, and the solution was then placed in an incubator at 37° C. for 10 minutes followed by sterile filtration to prepare a HEK-Blue detection medium. The compound was firstly formulated into a 20 mM stock solution, then diluted with pure DMSO to a maximum concentration of $6\times10^6$ nM, and a total of 10 points were obtained by a 3-fold gradient dilution.

The above formulated compound was firstly diluted 20-fold with the medium, then 20 μl of the diluted compound were added to each well. The supernate was removed from the HEK-Blue™ hTLR7 cells, to which 2-5 ml of pre-warmed PBS were then added. The cells were placed in an incubator for 1-2 minutes, gently pipetted, and counted by trypan blue staining. The cells were re-suspended in the HEK-Blue detection medium to adjust the concentration to $2.2\times10^5$ cells/ml. 180 μl of cells were added to the above 96-well plate already added with 20 μl of the compounds, and incubated at 37° C. for 6-16 hours.

The microplate reader read at a wavelength of 620 nm to obtain corresponding OD values, and the EC$_{50}$ values of the compounds was calculated by Graphpad Prism.

The activation effect of the compounds of the present invention on human TLR7 can be determined by the above test, and the obtained EC$_{50}$ values are shown in Table 1.

TABLE 1

| EC$_{50}$ of the compounds of the present invention on human TLR7 | | |
|---|---|---|
| Example No. | EC$_{50}$ (nM) | Emax (%) |
| 1 | 28 | 100 |
| 2 | 64 | 91 |
| 3 | 77 | 91 |
| 4 | 166 | 88 |
| 6 | 233 | 91 |
| 7 | 180 | 95 |

TABLE 1-continued

EC$_{50}$ of the compounds of the present
invention on human TLR7

| Example No. | EC$_{50}$ (nM) | Emax (%) |
| --- | --- | --- |
| 8 | 217 | 104 |
| 9 | 128 | 96 |
| 10 | 349 | 79 |
| 11 | 335 | 85 |
| 12 | 388 | 78 |

Conclusion: The compounds of the present invention have a significant activation effect on human TLR7.

Test Example 2. Determination of Agonistic Activity of the Compounds of the Present Invention on Human TLR8

The activation effect of the compounds of the present invention on the hTLR8 protein expressed by the HEK-Blue™ hTLR8 stably transfected cells was determined by the following experimental method:

I. Experimental Materials and Instruments
1. DMEM (Gibco, 10564-029),
2. Fetal bovine serum (GIBCO, 10099),
3. Penicillin-streptomycin (Gibco, 15140-122),
4. Trypan blue solution (Sigma, T8154-100ML),
5. Flexstation 3 multi-function microplate reader (Molecular Devices),
6. HEK-Blue™ HTLR8 cell line (InvivoGen, hkb-hTLR8),
7. HEK-Blue detection reagent (InvivoGen, hb-det3).

II. Experimental Procedures

A bag of HEK-Blue detection dry powder was dissolved in 50 ml of water free of endotoxin, and the solution was then placed in an incubator at 37° C. for 10 minutes followed by sterile filtration to prepare a HEK-Blue detection medium. The compound was firstly formulated into a 20 mM stock solution, then diluted with pure DMSO to a maximum concentration of 6×10$^6$ nM, and a total of 10 points were obtained by a 3-fold gradient dilution. The compound was firstly diluted 20-fold with the medium, then 20 μl of the diluted compound were added to each well.

The supernate was removed from the HEK-Blue™ hTLR8 cells, to which 2-5 ml of pre-warmed PBS were then added. The cells were placed in an incubator for 1-2 minutes, gently pipetted, and counted by trypan blue staining. The cells were re-suspended in the HEK-Blue detection medium to adjust the concentration to 2.2×10$^5$ cells/ml. 180 μl of cells were added to the above 96-well plate already added with 20 μl of the compounds, and incubated at 37° C. for 6-16 hours.

The microplate reader read at a wavelength of 620 nm to obtain corresponding OD values, and the EC$_{50}$ values of the compounds was calculated by Graphpad Prism.

The activation effect of the compounds of the present invention on human TLR8 can be determined by the above test, and the obtained EC$_{50}$ values are shown in Table 2.

TABLE 2

EC$_{50}$ of the compounds of the present
invention on human TLR8

| Example No. | EC$_{50}$ (μM) | Emax (%) |
| --- | --- | --- |
| 1 | >30 | 8 |
| 2 | >29 | 52 |

TABLE 2-continued

EC$_{50}$ of the compounds of the present
invention on human TLR8

| Example No. | EC$_{50}$ (μM) | Emax (%) |
| --- | --- | --- |
| 3 | >24 | 2 |
| 4 | >30 | 28 |
| 6 | >6 | 35 |
| 7 | >30 | 0 |
| 8 | >30 | 2 |
| 10 | >30 | 0 |
| 11 | >30 | 0 |
| 12 | >30 | 5 |

Conclusion: The compounds of the present invention have no activation effect on human TLR8, indicating that the compounds of the present invention have a high selectivity on TLR7.

Test Example 3. Determination of the Ability of the Compounds of the Present Invention to Stimulate the Secretion of IFN-α from Peripheral Blood Mononuclear Cells (PBMC)

The ability of the compounds of the present invention to stimulate the secretion of IFN-α from PBMC was determined by the following experimental method:

I. Experimental Materials and Instruments
1. RPMI 1640 (Invitrogen, 11875),
2. FBS (Gibco, 10099-141)
3. Penicillin-streptomycin (Gibco, 15140-122),
4. Ficoll-Paque PREMIUM (GE, 17-5442-02),
5. Trypan blue solution (Sigma, T8154-100ML),
6. SepMate™-50 (Stemcell, 15460),
7. Bright-Line™ blood cell counter (Sigma, Z359629-1EA),
8. Human IFN-α kit (cisbio, 6FHIFPEB),
9. PHERAStar multi-function microplate reader (BMG, PHERAStar).

II. Experimental Procedures

The compound was diluted with pure DMSO to a maximum concentration of 5 mM, and a total of 9 points were obtained by a 4-fold gradient dilution. 4 μl of the compound were then added to 196 μl of RPMI 1640 medium containing 10% FBS and mixed well. 50 μl of the mixture were taken from each well and added to a new 96-well plate.

All reagents were equilibrated to room temperature. 60 ml of blood and PBS+2% FBS were added to a 250 ml culture flask, gently pipetted, mixed well and diluted. 15 ml of lymphocyte separation solution Ficoll-Paque PREMIUM and then 30 ml of diluted blood were added to a 50 ml PBMC centrifuge tube SepMate™-50. The mixture was centrifuged at 1200 g for 10 minutes at room temperature. The supernatant was taken and then centrifuged at 300 g for 8 minutes. The cells were re-suspended in the RMPI 1640 medium containing 10% FBS and counted, and the number of PBMCs was adjusted to 3.33×10$^6$ cells/ml. 150 μl of the cell solution were added to the plate added with the compound, and incubated in an incubator at 37° C., in 5.0% CO$_2$ for 24 hours.

The cell culture plate was placed in a centrifuge, and centrifuged at 1200 rpm for 10 minutes at room temperature. 150 μl of the supernatant were taken from each well. The reagents in the human IFN-α kit were first equilibrated to normal temperature. The anti-IFN-α-Eu$^{3+}$-Cryptate conjugate and the anti-IFN-α-d2-conjugate were formulated in the dark according to the kit instructions, and both of them were mixed well with the conjugate buffer at a ratio of 1:40. 16 µl of the supernatant obtained by centrifugation were then added to each well. 2 µl of anti-IFN-α-Eu$^{3+}$-Cryptate conjugate and anti-IFN-α-d2-conjugate formulated just now were then added to each well. The plate was shaken and mixed well, and incubated in the dark at room temperature for 3 hours.

The PHERAStar was read in the HTRF mode. The lowest compound concentration that stimulated cytokine levels of at least 3 times higher than the minimum detection limit was defined as the minimal effective concentration (MEC) value of the compound in the cytokine stimulation test.

The ability of the compounds of the present invention to stimulate the secretion of IFN-α from PBMC was determined by the above test, and the obtained MEC values are shown in Table 3.

TABLE 3

MEC of the compounds of the present invention to stimulate the secretion of IFN-α from PBMC

| Example No. | MEC (nM) |
|---|---|
| 1 | 6 |
| 2 | 23 |
| 3 | 20 |
| 4 | 100 |
| 5 | 41 |
| 7 | 89 |

Conclusion: It can be seen from the data of activity of stimulating the secretion of IFN-α from PBMC that the compounds of the present invention have an advantage of lower effective concentration.

Test Example 4. Inhibition Effect of the Compounds of the Present Invention on the Enzyme Activity of Midazolam Metabolite Site of CYP3A4 in Human Liver Microsomes The effect of the compounds of the present invention on the enzyme activity of midazolam metabolite site of CYP3A4 in human liver microsomes was determined by the following experimental method:

I. Experimental Materials and Instruments
1. Phosphate buffer (PBS),
2. NADPH (Sigma N-1630),
3. Human liver microsome (Corning Gentest),
4. ABI QTrap 4000 liquid chromatograph/mass spectrometer (AB Sciex),
5. Inertsil C8-3 column, 4.6×50 mm, 5 µm (Dikma Technologies Inc., USA),
6. CYP probe substrate (midazolam/10 µM) and positive control inhibitor (ketoconazole).

II. Experimental Procedures 100 mM PBS buffer was formulated, which was then used to formulate 2.5 mg/ml microsome solution and 5 mM NADPH solution. The 5× concentration of the compound working solution was diluted with PBS gradient (150, 50, 15, 5, 1.5, 0.15, 0.015, 0 µM). The 5× concentration of ketoconazole working solution was diluted with PBS gradient (150, 50, 15, 5, 1.5, 0.15, 0.015, 0 µM). Dextromethorphan working solution was diluted with PBS to a concentration of 50 µM.

20 µl of 2.5 mg/ml microsome solution, 20 µl of 50 µM testosterone working solution, 20 µl of MgCl$_2$ solution and 20 µl of the compound working solution (150, 50, 15, 5, 1.5, 0.15, 0.015, 0 µM, different reaction systems for each concentration) were taken respectively and mixed well. For the positive control group, the compound was replaced with the same concentration of ketoconazole. The mixture together with 5 mM NADPH solution were pre-incubated at 37° C. for 5 minutes. After 5 minutes, 20 µl of NADPH were added to each well, the reaction was started and incubated for 30 minutes. All the incubated samples were present in duplicate. After 30 minutes, 250 µl of acetonitrile containing internal standard were added to all samples, mixed well, shaken at 800 rpm for 10 minutes, and then centrifuged at 3700 rpm for 10 minutes. 80 µl of the supernatant were taken and analyzed by LC-MS/MS.

The data were calculated by Graphpad Prism to obtain the IC$_{50}$ values of the compounds on the midazolam metabolite site of CYP3A4.

IC$_{50}$ values of the compounds of the present invention on the midazolam metabolite site of CYP3A4 in human liver microsomes.

| Example No. | IC$_{50}$ (µM) |
|---|---|
| 1 | 14 |
| 2 | 10 |
| 3 | 7 |
| 4 | 11 |
| 6 | 10 |
| 7 | >30 |
| 12 | 16 |

Conclusion: The compounds of the present invention have a weak inhibition effect on the midazolam metabolic site of CYP3A4 in human liver microsome, and show better safety, indicating that the metabolic drug interaction based on the midazolam metabolic site of CYP3A4 will not occur.

Test Example 5. Inhibition Effect of the Compounds of the Present Invention on the Enzyme Activity of CYP2D6 in Human Liver Microsomes The effect of the compounds of the present invention on the enzyme activity of CYP2D6 in human liver microsomes was determined by the following experimental method:

I. Experimental materials and instruments
1. Phosphate buffer (PBS),
2. NADPH (Sigma N-1630),
3. Human liver microsome (Corning Gentest),
4. ABI QTrap 4000 liquid chromatograph/mass spectrometer (AB Sciex),
5. Inertsil C8-3 column, 4.6×50 mm, 5 µm (Dikma Technologies Inc., USA),
6. CYP probe substrate (dextromethorphan/10 µM) and positive control inhibitor (quinidine).

II. Experimental Procedures 100 mM PBS buffer was formulated, which was then used to formulate 2.5 mg/ml microsome solution and 5 mM NADPH solution. The 5× concentration of the compound working solution was diluted with PBS gradient (150, 50, 15, 5, 1.5, 0.15, 0.015, 0 µM). The 5× concentration of quinidine working solution was diluted with PBS gradient (150, 50, 15, 5, 1.5, 0.15, 0.015, 0 µM). Dextromethorphan working solution was diluted with PBS to a concentration of 50 µM.

20 µl of 2.5 mg/ml microsome solution, 20 µl of 50 µM testosterone working solution, 20 µl of MgCl$_2$ solution and 20 µl of the compound working solution (150, 50, 15, 5, 1.5, 0.15, 0.015, 0 µM, different reaction systems for each concentration) were taken respectively and mixed well. For the positive control group, the compound was replaced with the same concentration of quinidine. The mixture together with 5 mM NADPH solution were pre-incubated at 37° C. for 5 minutes. After 5 minutes, 20 µl of NADPH were added to each well, the reaction was started and incubated for 30 minutes. All the incubated samples were present in duplicate. After 30 minutes, 250 µl of acetonitrile containing internal standard were added to all samples, mixed well, shaken at 800 rpm for 10 minutes, and then centrifuged at 3700 rpm for 10 minutes. 80 µl of the supernatant were taken and analyzed by LC-MS/MS.

The data were calculated by Graphpad Prism to obtain the $IC_{50}$ values of the compounds on the metabolite site of CYP2D6.

$IC_{50}$ values of the compounds of the present invention for no inhibition on CYP2D6 in human liver microsomes.

| Example No. | $IC_{50}$ (µM) |
|---|---|
| 1 | >30 |
| 2 | >30 |
| 3 | 4 |
| 4 | 16 |
| 6 | 10 |
| 7 | >30 |
| 12 | 16 |

Conclusion: The compounds of the present invention have a weak inhibition effect on the enzyme activity of CYP2D6 in human liver microsomes, and show better safety, indicating that the metabolic drug interaction based on CYP2D6 will not occur.

Test Example 6. Inhibition Effect of the Compounds of the Present Invention on the Enzyme Activity of Testosterone Metabolite Site of CYP3A4 in Human Liver Microsomes The effect of the compounds of the present invention on the enzyme activity of testosterone metabolite site of CYP3A4 in human liver microsomes was determined by the following experimental method:

I. Experimental Materials and Instruments
1. Phosphate buffer (PBS),
2. NADPH (Sigma N-1630),
3. Human liver microsome (Corning Gentest),
4. ABI QTrap 4000 liquid chromatograph/mass spectrometer (AB Sciex),
5. Inertsil C8-3 column, 4.6×50 mm, 5 µm (Dikma Technologies Inc., USA),
6. CYP probe substrate (testosterone/10 µM) and positive control inhibitor (ketoconazole).

II. Experimental Procedures
100 mM PBS buffer was formulated, which was then used to formulate 2.5 mg/ml microsome solution and 5 mM NADPH solution. The 5× concentration of the compound working solution was diluted with PBS gradient (150, 50, 15, 5, 1.5, 0.15, 0.015, 0 µM). The 5× concentration of ketoconazole working solution was diluted with PBS gradient (150, 50, 15, 5, 1.5, 0.15, 0.015, 0 µM). Dextromethorphan working solution was diluted with PBS to a concentration of 50 µM.

20 µl of 2.5 mg/ml microsome solution, 20 µl of 50 µM testosterone working solution, 20 µl of MgCl$_2$ solution and 20 µl of the compound working solution (150, 50, 15, 5, 1.5, 0.15, 0.015, 0 µM, different reaction systems for each concentration) were taken respectively and mixed well. For the positive control group, the compound was replaced with the same concentration of ketoconazole. The mixture together with 5 mM NADPH solution were pre-incubated at 37° C. for 5 minutes. After 5 minutes, 20 µl of NADPH were added to each well, the reaction was started and incubated for 30 minutes. All the incubated samples were present in duplicate. After 30 minutes, 250 µl of acetonitrile containing internal standard were added to all samples, mixed well, shaken at 800 rpm for 10 minutes, and then centrifuged at 3700 rpm for 10 minutes. 80 µl of the supernatant were taken and analyzed by LC-MS/MS.

The data were calculated by Graphpad Prism to obtain the $IC_{50}$ values of the compounds on the testosterone metabolite site of CYP3A4.

$IC_{50}$ values of the compounds of the present invention on the testosterone metabolite site of CYP3A4 in human liver microsomes.

| Example No. | $IC_{50}$ (µM) |
|---|---|
| 1 | 4 |
| 2 | 19 |
| 3 | 3 |
| 4 | 6 |
| 6 | 3 |
| 7 | >30 |
| 12 | >30 |

Conclusion: The compounds of the present invention have a weak inhibition on the testosterone metabolite site of CYP3A4 in human liver microsomes, and show better safety.

What is claimed is:
1. A compound of formula (I):

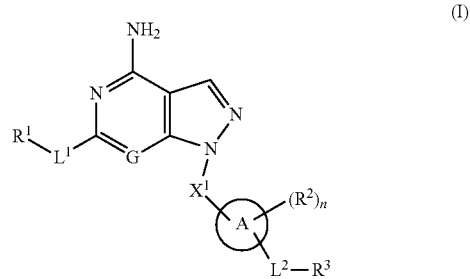

or a tautomer, mesomer, racemate, enantiomer, diastereomer thereof, or mixture thereof, or a pharmaceutically acceptable salt thereof,
wherein:
ring A is selected from the group consisting of cycloalkyl, heterocyclyl, aryl and heteroaryl;
G is CH or N;
$X^1$ is alkylene or $S(O)_m$, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;
$L^1$ is selected from the group consisting of —NR$^4$—, —O—, —S—, —C(O)—, —S(O)$_m$—, —N(R$^4$)C(O)—, —C(O)N(R$^4$)—, —N(R$^4$)S(O)$_2$—, —S(O)$_2$N(R$^4$)— and a covalent bond;

R¹ is selected from the group consisting of alkyl, alkoxy, haloalkyl, alkenyl, alkynyl, cycloalkyl, heterocyclyl, aryl and heteroaryl, wherein the alkyl, alkenyl, alkynyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR⁵, —C(O)R⁵, —S(O)$_m$R⁵, —NR⁶R⁷ and —C(O)NR⁶R⁷;

each R² is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR⁵, —C(O)R⁵, —S(O)$_m$R⁵, —NR⁶R⁷ and —C(O)NR⁶R⁷;

L² is alkylene, wherein the alkylene is optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR⁵, —C(O)R⁵, —S(O)$_m$R⁵, —NR⁶R⁷ and —C(O)NR⁶R⁷;

R³ is selected from the group consisting of haloalkyl, hydroxy, hydroxyalkyl, cyano, amino, nitro, cycloalkyl, heterocyclyl, aryl, heteroaryl, —OR⁵, —C(O)R⁵, —S(O)$_m$R⁵, —NR⁶R⁷ and —C(O)NR⁶R⁷, wherein the cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR⁸, —C(O)R⁸, —S(O)$_m$R⁸, —NR⁹R¹⁰ and —C(O)NR⁹R¹⁰;

R⁴ is selected from the group consisting of hydrogen, alkyl, haloalkyl, cycloalkyl, heterocyclyl, aryl and heteroaryl;

R⁵ is selected from the group consisting of hydrogen, alkyl, haloalkyl, amino, hydroxy, cycloalkyl, heterocyclyl, aryl and heteroaryl;

R⁶ and R⁷ are identical or different and are each independently selected from the group consisting of hydrogen, alkyl, haloalkyl, cycloalkyl, heterocyclyl, aryl, heteroaryl, —C(O)R⁸, —S(O)$_m$R⁸ and —C(O)NR⁹R¹⁰, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, R⁶ and R⁷ together with the nitrogen atom to which they are attached form a heterocyclyl, wherein the heterocyclyl optionally contains one or two identical or different heteroatoms selected from the group consisting of N, O and S in addition to the nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

R⁸ is selected from the group consisting of hydrogen, alkyl, haloalkyl, amino, hydroxy, cycloalkyl, heterocyclyl, aryl and heteroaryl;

R⁹ and R¹⁰ are identical or different and are each independently selected from the group consisting of hydrogen, alkyl, haloalkyl, amino, hydroxy, cycloalkyl, heterocyclyl, aryl and heteroaryl;

n is 0, 1, 2, 3 or 4;

m is 0, 1 or 2;

said cycloalkyl refers to a saturated or partially unsaturated monocyclic or polycyclic hydrocarbon group having 3 to 20 carbon atoms, and the polycyclic cycloalkyl comprises a cycloalkyl having a spiro ring, fused ring or bridged ring;

said heterocyclyl refers to a 3 to 20 membered saturated or partially unsaturated monocyclic or polycyclic hydrocarbon substituent group having 1 to 4 heteroatoms selected from the group consisting of N, O, S(O) and S(O)$_2$, and the polycyclic heterocyclyl comprises a heterocyclyl having a spiro ring, fused ring or bridged ring; and said heteroaryl refers to a 5 to 14 membered heteroaromatic system having 1 to 4 heteroatoms selected from the group consisting of O, S and N.

2. The compound according to claim 1, wherein R³ is heterocyclyl, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl.

3. The compound according to claim 1, wherein R³ is —NR⁶R⁷, and R⁶ and R⁷ together with the nitrogen atom to which they are attached form a heterocyclyl, wherein the heterocyclyl optionally contains one or two identical or different heteroatoms selected from the group consisting of N, O and S in addition to the nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl.

4. The compound according to claim 1, wherein the ring A is phenyl.

5. The compound according to claim 1, wherein X¹ is alkylene.

6. The compound according to claim 1, being a compound of formula (II):

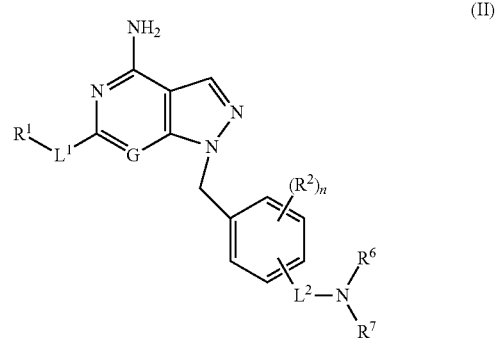

or a tautomer, mesomer, racemate, enantiomer, diastereomer thereof, or mixture thereof, or a pharmaceutically acceptable salt thereof.

7. The compound according to claim 1, wherein G is N.

8. The compound according to claim 1, wherein L² is alkylene.

9. The compound according to claim 1, being a compound of formula (III):

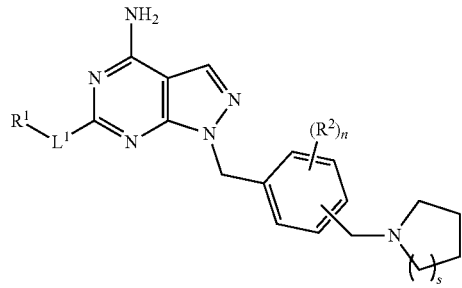

(III)

or a tautomer, mesomer, racemate, enantiomer, diastereomer thereof, or mixture thereof, or a pharmaceutically acceptable salt thereof, wherein:

s is 0, 1 or 2.

10. The compound according to claim 1, wherein $L^1$ is selected from the group consisting of —O—, —$NR^4$—, —C(O)— and —C(O)N($R^4$)—, and $R^4$ is hydrogen or alkyl.

11. The compound according to claim 1, wherein $R^1$ is alkyl optionally substituted by one or more alkoxy.

12. The compound according to claim 1, wherein each $R^2$ is identical or different and each is independently hydrogen or halogen.

13. A compound selected from the group consisting of:

1

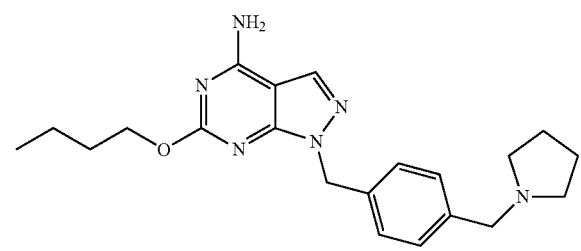

2

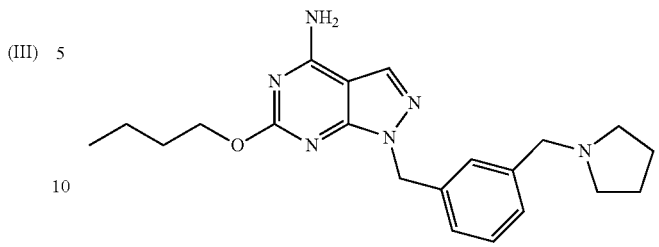

3

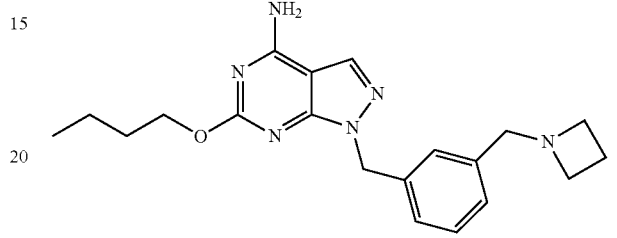

4

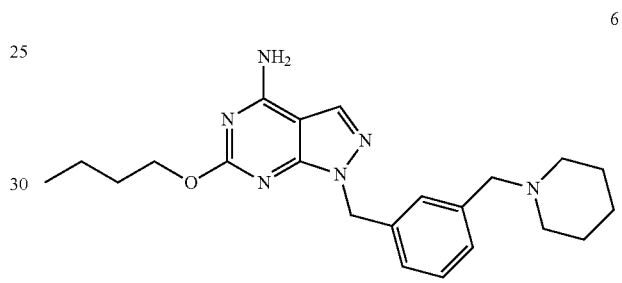

5

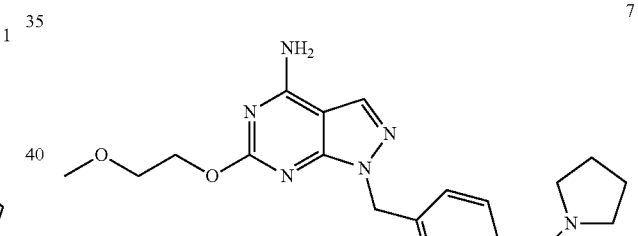

6

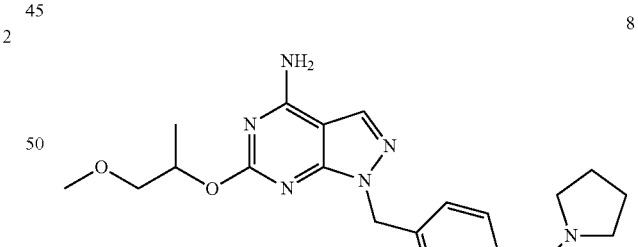

7

8

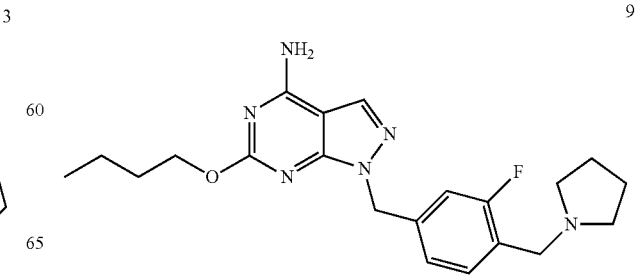

9

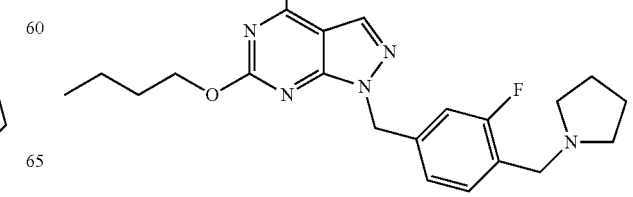

-continued

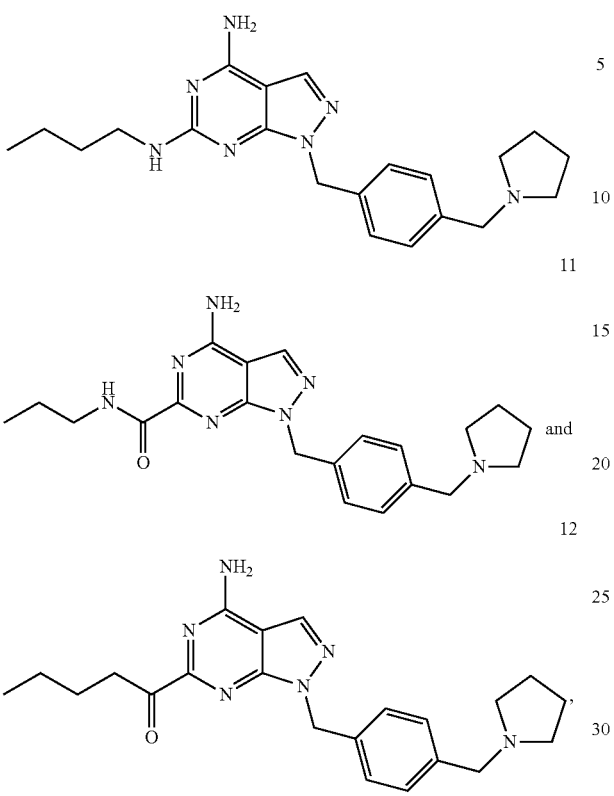

or a tautomer, mesomer, racemate, enantiomer, diastereomer thereof, or mixture thereof, or a pharmaceutically acceptable salt thereof.

14. A compound of formula (I-C):

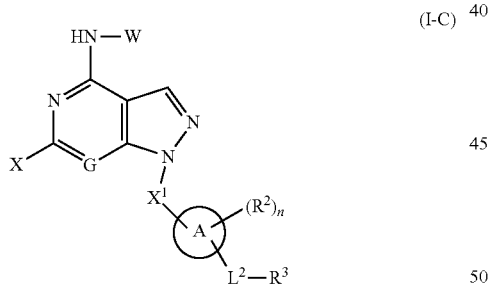

(I-C)

or a tautomer, mesomer, racemate, enantiomer, diastereomer thereof, or mixture thereof, or a pharmaceutically acceptable salt thereof,
wherein:
W is an amino protecting group;
X is halogen;
ring A is selected from the group consisting of cycloalkyl, heterocyclyl, aryl and heteroaryl;
G is CH or N;
$X^1$ is alkylene or $S(O)_m$, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;
each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, —$NR^6R^7$ and —$C(O)NR^6R^7$;
$L^2$ is alkylene, wherein the alkylene is optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, —$NR^6R^7$ and —$C(O)NR^6R^7$;
$R^3$ is selected from the group consisting of haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, —$NR^6R^7$ and —$C(O)NR^6R^7$, wherein the cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —$OR^8$, —$C(O)R^8$, —$S(O)_mR^8$, —$NR^9R^{10}$ and —$C(O)NR^9R^{10}$;
$R^5$ is selected from the group consisting of hydrogen, alkyl, haloalkyl, amino, hydroxy, cycloalkyl, heterocyclyl, aryl and heteroaryl;
$R^6$ and $R^7$ are identical or different and are each independently selected from the group consisting of hydrogen, alkyl, haloalkyl, cycloalkyl, heterocyclyl, aryl, heteroaryl, —$C(O)R^8$, —$S(O)_mR^8$ and —$C(O)NR^9R^{10}$, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;
or, $R^6$ and $R^7$ together with the nitrogen atom to which they are attached form a heterocyclyl, wherein the heterocyclyl optionally contains one or two identical or different heteroatoms selected from the group consisting of N, O and S in addition to the nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;
$R^8$ is selected from the group consisting of hydrogen, alkyl, haloalkyl, amino, hydroxy, cycloalkyl, heterocyclyl, aryl and heteroaryl;
$R^9$ and $R^{10}$ are identical or different and are each independently selected from the group consisting of hydrogen, alkyl, haloalkyl, amino, hydroxy, cycloalkyl, heterocyclyl, aryl and heteroaryl;
n is 0, 1, 2, 3 or 4;
m is 0, 1 or 2;
said cycloalkyl refers to a saturated or partially unsaturated monocyclic or polycyclic hydrocarbon group having 3 to 20 carbon atoms, and the polycyclic cycloalkyl comprises a cycloalkyl having a spiro ring, fused ring or bridged ring;
said heterocyclyl refers to a 3 to 20 membered saturated or partially unsaturated monocyclic or polycyclic hydrocarbon substituent group having 1 to 4 heteroatoms selected from the group consisting of N, O, S(O)

and S(O)₂, and the polycyclic heterocyclyl comprises a heterocyclyl having a spiro ring, fused ring or bridged ring; and said heteroaryl refers to a 5 to 14 membered heteroaromatic system having 1 to 4 heteroatoms selected from the group consisting of O, S and N.

15. The compound according to claim 14, wherein the compound is selected from the group consisting of:

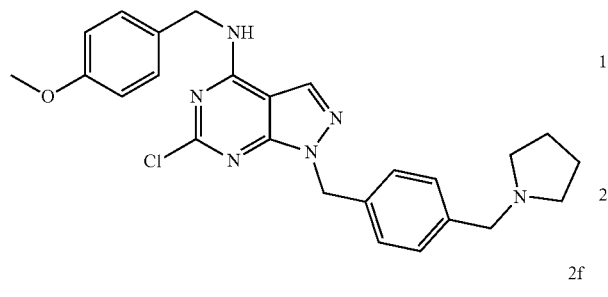
1e

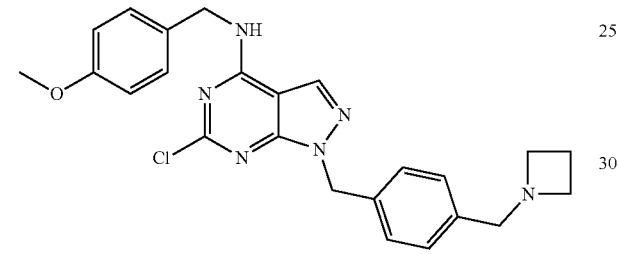
2f

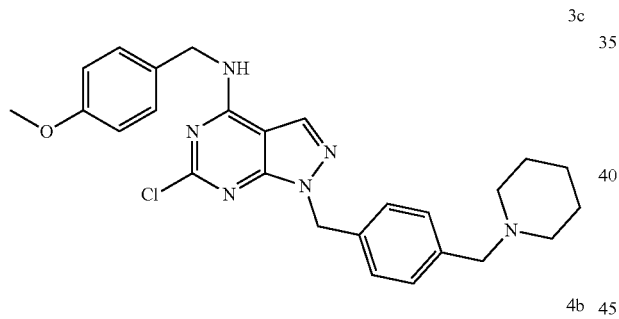
3c

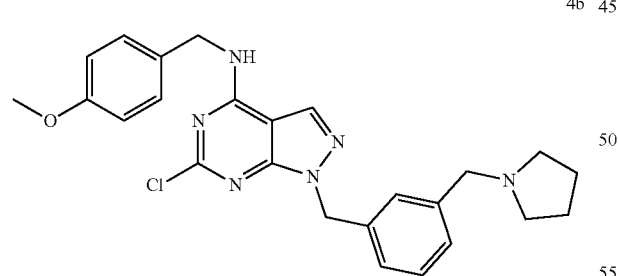
4b

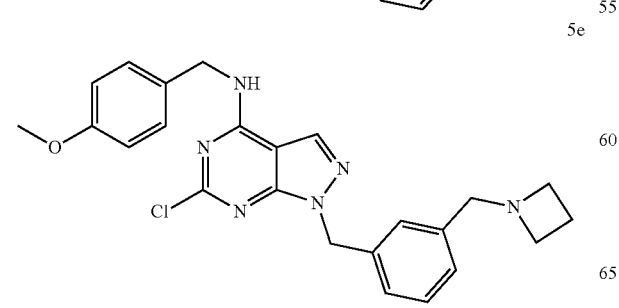
5e

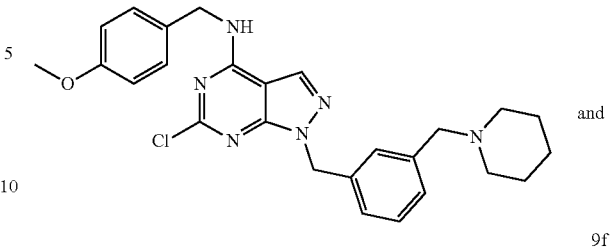
6c and

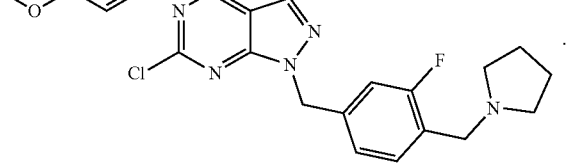
9f

16. A compound of formula (I-E):

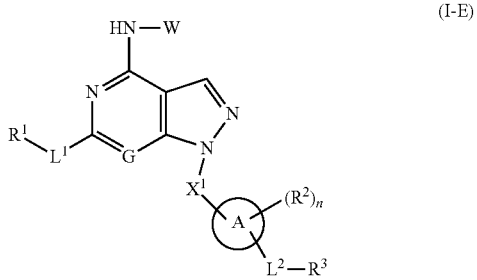
(I-E)

or a tautomer, mesomer, racemate, enantiomer, diastereomer thereof, or mixture thereof, or a pharmaceutically acceptable salt thereof, wherein:
W is an amino protecting group;
ring A is selected from the group consisting of cycloalkyl, heterocyclyl, aryl and heteroaryl;
G is CH or N;
$X^1$ is alkylene or $S(O)_m$, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;
$L^1$ is selected from the group consisting of —NR⁴—, —O—, —S—, —C(O)—, S(O)ₘ-, —N(R⁴)C(O)—, —C(O)N(R⁴)—, —N(R⁴)S(O)₂-, —S(O)₂N(R⁴)— and a covalent bond;
$R^1$ is selected from the group consisting of alkyl, alkoxy, haloalkyl, alkenyl, alkynyl, cycloalkyl, heterocyclyl, aryl and heteroaryl, wherein the alkyl, alkenyl, alkynyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR⁵,—C(O)R⁵, —S(O)ₘR⁵, —NR⁶R⁷ and —C(O)NR⁶R⁷;
each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$;

L$^2$ is alkylene, wherein the alkylene is optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$;

R$^3$ is selected from the group consisting of haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, —NR$^6$R$^7$ and —C(O)NR$^6$R$^7$, wherein the cycloalkyl, heterocyclyl, aryl and heteroaryl are each independently optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —OR$^8$, —C(O)R$^8$, —S(O)$_m$R$^8$, —NR$^9$R$^{10}$ and —C(O)NR$^9$R$^{10}$;

R$^4$ is selected from the group consisting of hydrogen, alkyl, haloalkyl, cycloalkyl, heterocyclyl, aryl and heteroaryl;

R$^5$ is selected from the group consisting of hydrogen, alkyl, haloalkyl, amino, hydroxy, cycloalkyl, heterocyclyl, aryl and heteroaryl;

R$^6$ and R$^7$ are identical or different and are each independently selected from the group consisting of hydrogen, alkyl, haloalkyl, cycloalkyl, heterocyclyl, aryl, heteroaryl, —C(O)R$^8$, —S(O)$_m$R$^8$ and —C(O)NR$^9$R$^{10}$, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, R$^6$ and R$^7$ together with the nitrogen atom to which they are attached form a heterocyclyl, wherein the heterocyclyl optionally contains one or two identical or different heteroatoms selected from the group consisting of N, O and S in addition to the nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

R$^8$ is selected from the group consisting of hydrogen, alkyl, haloalkyl, amino, hydroxy, cycloalkyl, heterocyclyl, aryl and heteroaryl;

R$^9$ and R$^{10}$ are identical or different and are each independently selected from the group consisting of hydrogen, alkyl, haloalkyl, amino, hydroxy, cycloalkyl, heterocyclyl, aryl and heteroaryl;

n is 0, 1, 2, 3 or 4;

m is 0, 1 or said cycloalkyl refers to a saturated or partially unsaturated monocyclic or polycyclic hydrocarbon group having 3 to 20 carbon atoms, and the polycyclic cycloalkyl comprises a cycloalkyl having a spiro ring, fused ring or bridged ring;

said heterocyclyl refers to a 3 to 20 membered saturated or partially unsaturated monocyclic or polycyclic hydrocarbon substituent group having 1 to 4 heteroatoms selected from the group consisting of N, O, S(O) and S(O)$_2$, and the polycyclic heterocyclyl comprises a heterocyclyl having a spiro ring, fused ring or bridged ring; and said heteroaryl refers to a 5 to 14 membered heteroaromatic system having 1 to 4 heteroatoms selected from the group consisting of O, S and N.

17. The compound according to claim 16, wherein the compound is selected from the group consisting of:

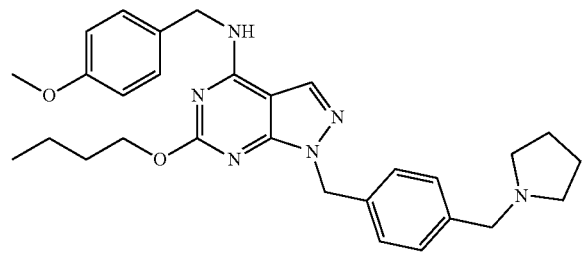

1f

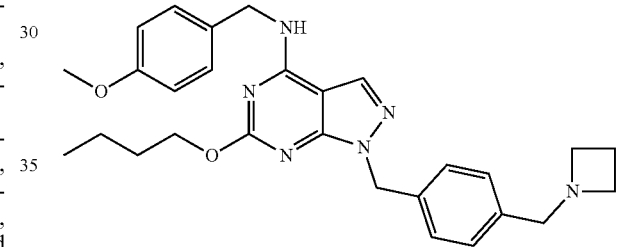

2g

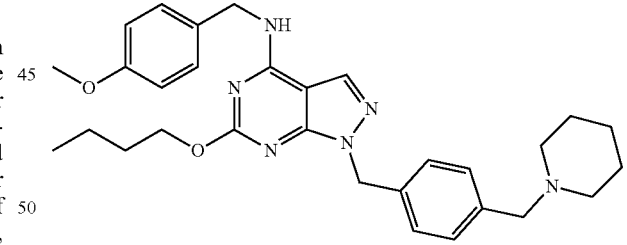

3d

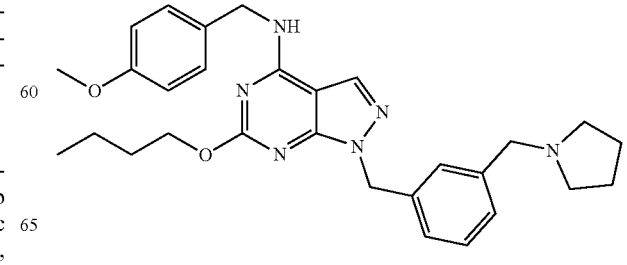

4c

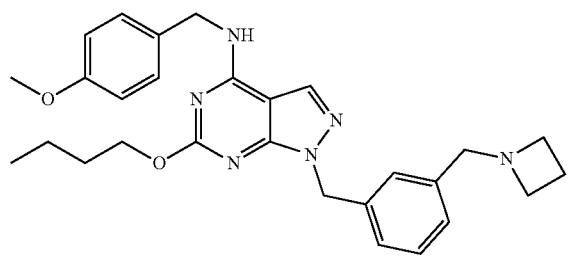
5f
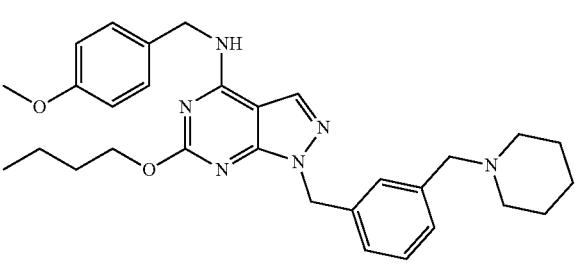
6d
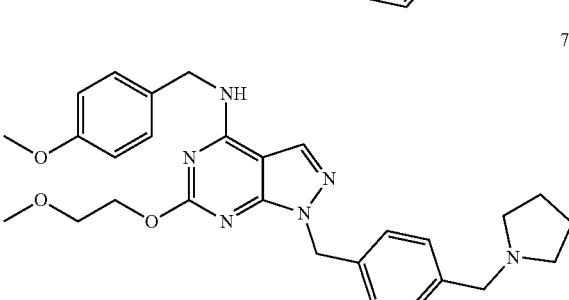
7a
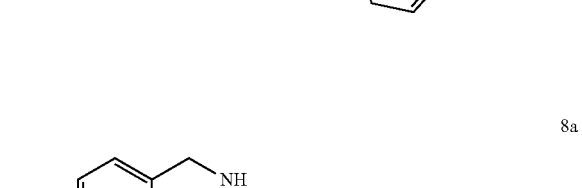
8a
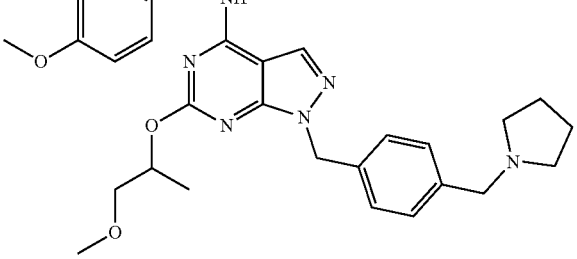
9g
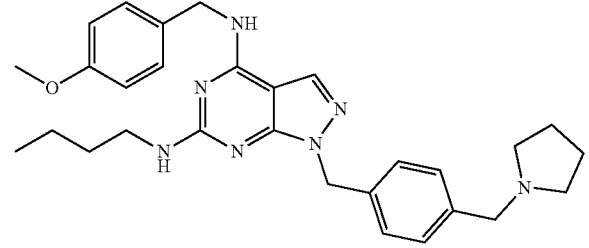
10a
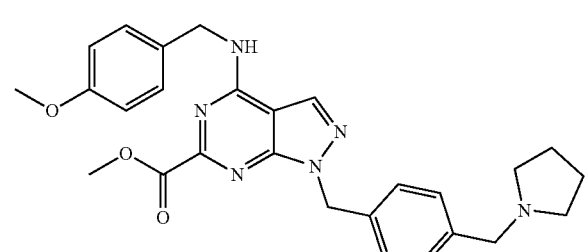
11a
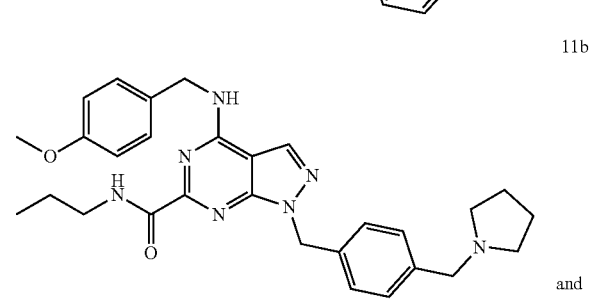
11b
and
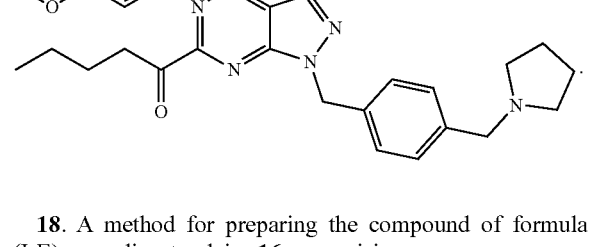
12b
18. A method for preparing the compound of formula (I-E) according to claim 16, comprising:
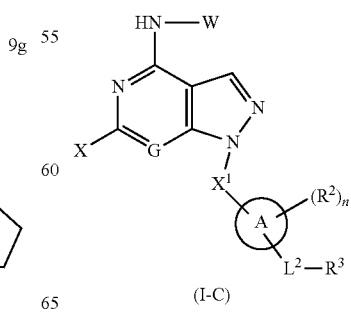
(I-C)
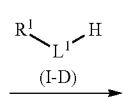
(I-D)

-continued

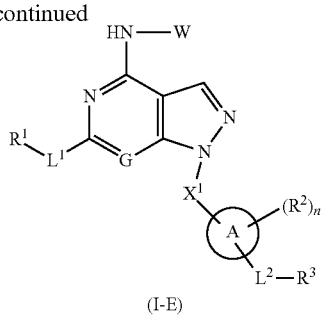

(I-E)

subjecting a compound of formula (I-C) and a compound of formula (I-D) to a nucleophilic substitution reaction under an alkaline condition to obtain the compound of formula (I-E);
wherein:
X is halogen.

19. A method for preparing the compound of formula (I) according to claim 1, comprising:

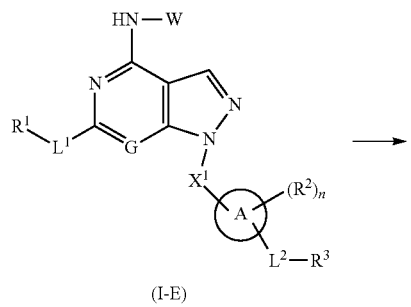

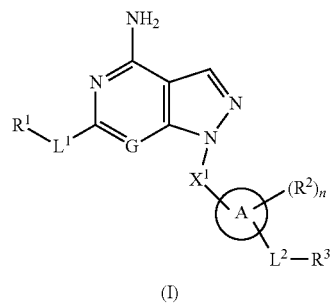

(I)

removing an amino protecting group of a compound of formula (I-E) under an acidic condition to obtain the compound of formula (I);
wherein:
W is the amino protecting group.

20. A pharmaceutical composition, comprising the compound, or a tautomer, mesomer, racemate, enantiomer, diastereomer thereof, or mixture thereof, or a pharmaceutically acceptable salt thereof according to claim 1, and one or more pharmaceutically acceptable carriers, diluents or excipients.

21. The compound according to claim 13, wherein the compound is

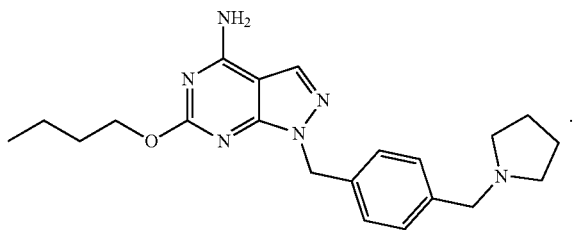

1

22. The compound according to claim 13, wherein the compound is

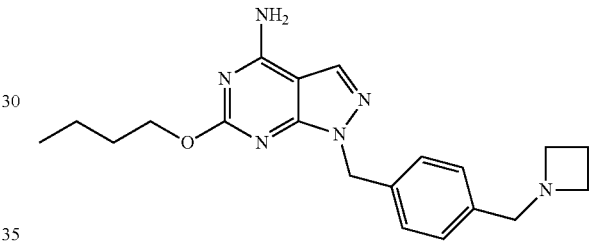

2

23. The compound according to claim 13, wherein the compound is

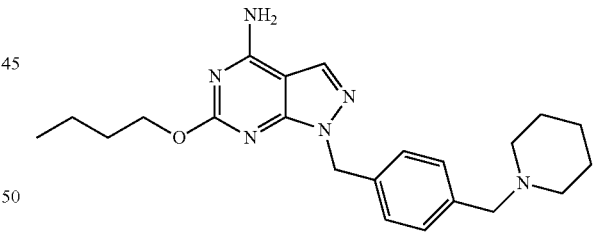

3

* * * * *